(12) United States Patent
Martin et al.

(10) Patent No.: US 10,665,349 B2
(45) Date of Patent: May 26, 2020

(54) METHODS FOR DETERMINING RISK AND TREATING DISEASES AND CONDITIONS THAT CORRELATE TO WEATHER DATA

(71) Applicants: Vincent Martin, Mason, OH (US); Linda Levin, Cincinnati, OH (US); Mark Russell Simmons, Cincinnati, OH (US); Robert Allen Nicholson, Chesterfield, MO (US); Albert Peterlin, Camp Hill, PA (US)

(72) Inventors: Vincent Martin, Mason, OH (US); Linda Levin, Cincinnati, OH (US); Mark Russell Simmons, Cincinnati, OH (US); Robert Allen Nicholson, Chesterfield, MO (US); Albert Peterlin, Camp Hill, PA (US)

(73) Assignees: University of Cincinnati, Cincinnati, OH (US); Errex, Inc., Camp Hill, PA (US)

( * ) Notice: Subject to any disclaimer, the term of this patent is extended or adjusted under 35 U.S.C. 154(b) by 623 days.

(21) Appl. No.: 15/508,507

(22) PCT Filed: Sep. 4, 2015

(86) PCT No.: PCT/US2015/048537
§ 371 (c)(1),
(2) Date: Mar. 3, 2017

(87) PCT Pub. No.: WO2016/037055
PCT Pub. Date: Mar. 10, 2016

(65) Prior Publication Data
US 2017/0308672 A1     Oct. 26, 2017

Related U.S. Application Data

(60) Provisional application No. 62/046,681, filed on Sep. 5, 2014.

(51) Int. Cl.
*G16H 50/30* (2018.01)
*G16H 50/70* (2018.01)
(Continued)

(52) U.S. Cl.
CPC ............ *G16H 50/30* (2018.01); *G06F 17/11* (2013.01); *G06F 19/00* (2013.01); *G06F 30/20* (2020.01);
(Continued)

(58) Field of Classification Search
CPC ........ G06Q 30/02; G06Q 30/06; G16H 10/20; G16H 20/10; G16H 20/30; G16H 20/70; G16H 40/67; G16H 50/30; G16H 50/80
See application file for complete search history.

(56) References Cited

U.S. PATENT DOCUMENTS

2006/0199239 A1* 9/2006 Gurbel .................... C12Q 1/56
                                                        435/11
2008/0086520 A1* 4/2008 Epelbaum .............. G06F 17/18
                                                        708/520
(Continued)

OTHER PUBLICATIONS

Koenker et al., "Quantile Regression: An Introduction" Journal of Economic Perspectives "Symposium on Econometric Tools". Sep. 27, 2013 (Year: 2013).*

(Continued)

*Primary Examiner* — Neal Sereboff
(74) *Attorney, Agent, or Firm* — Dinsmore & Shohl LLP

(57) ABSTRACT

Methods and model equations are provided for predicting a risk of a subject who experiences adverse medical events associated with the weather, of experiencing a new-onset event. Methods include a) identifying a climate region of interest; b) collecting daily mean barometric pressure (BP) data for a time frame and dividing the days of the time frame
(Continued)

into at least upper, middle and lower quantile BP days to identify the upper quantile BP days.

4 Claims, 16 Drawing Sheets

(51) Int. Cl.
    *G16H 50/50*     (2018.01)
    *G06F 30/20*     (2020.01)
    *G16H 40/20*     (2018.01)
    *G06F 17/11*     (2006.01)
    *G06F 111/10*     (2020.01)
    *G01W 1/02*     (2006.01)
    *G06F 19/00*     (2018.01)

(52) U.S. Cl.
    CPC ............. *G16H 40/20* (2018.01); *G16H 50/50* (2018.01); *G16H 50/70* (2018.01); *G01W 1/02* (2013.01); *G06F 2111/10* (2020.01); *Y02A 90/22* (2018.01); *Y02A 90/26* (2018.01)

(56) References Cited

U.S. PATENT DOCUMENTS

| | | | |
|---|---|---|---|
| 2008/0188720 A1* | 8/2008 | McAlindon | G16H 10/20 600/300 |
| 2012/0232926 A1* | 9/2012 | Boyle | G06Q 10/04 705/3 |
| 2014/0114677 A1* | 4/2014 | Holmes | G06F 19/3418 705/2 |

OTHER PUBLICATIONS

A. Peel, B.L. Finlayson; T. McMahon, "Updated World Map of the Koppen-Geiger Climate Classification," Hydrol. Earth Syst. Sci., 11: 1633-1644, 2007.

* cited by examiner

FIG. 5B

| MODEL | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|
| CUT-POINTS | BP_diff Mean ≤ 0.0 | Yes vs. No | 3.23 | 1.32 | 7.93 | 0.01 | 15800.25 | 15414.02 |
| | WS_diff Max ≥ 7 | Yes vs. No | 2.65 | 1.51 | 4.62 | <0.01 | | |

FIG. 5C

MODEL 1

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Mean ≤ 0.0 | Yes vs. No | 3.24 (2.83, 3.78) | 1.32 (1.20, 1.47) | 7.99 (6.67, 9.71) | 0.01 (0.01, 0.02) | 15,842.19 (14,647.72, 17,099.64) |
| | WS_diff Max ≥ 7 | Yes vs. No | 2.65 (2.57, 2.73) | 1.51 (1.47, 1.56) | 4.63 (4.50, 4.79) | <0.01 (<0.01, <0.01) | |

MODEL 2

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Mean ≤ -0.1 | Yes vs. No | 3.22 (3.07, 3.37) | 1.77 (1.71, 1.82) | 5.85 (5.51, 6.23) | <0.01 (<0.01, <0.01) | 15,644.40 (14,459.07, 16,878.65) |
| | WS_diff Max ≥ 7 | Yes vs. No | 2.07 (1.99, 2.14) | 1.21 (1.15, 1.26) | 3.53 (3.41, 3.66) | 0.01 (<0.01, 0.01) | |

| MODEL | | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|---|
| CUT-POINTS | | BP_diff Mean ≤ 0.0 | Yes vs. No | 2.10 | 0.91 | 4.85 | 0.08 | 6,591.37 | 6,306.79 |
| | | WS_diff Max ≥ 6 | Yes vs. No | 2.25 | 0.93 | 5.45 | 0.07 | | |

FIG. 6B

| MODEL | | PARAMETER | VARIABLE | RR | LOWER 95% CI | UPPER 95% CI | P-VALUE | QIC FIT STATISTIC |
|---|---|---|---|---|---|---|---|---|
| | | | | | | | | MODEL 1 |
| CUT-POINTS | | BP_diff Mean ≤ 0.0 | Yes vs. No | 2.09 (1.99, 2.19) | 0.90 (0.86, 0.94) | 4.87 (4.61, 5.14) | 0.09 (0.07, 0.11) | 6,59.36 (6,201.21, 6,991.03) |
| | | WS_diff Max ≥ 6 | Yes vs. No | 2.26 (2.07, 2.47) | 0.93 (0.86, 1.00) | 5.49 (4.94, 63.13) | 0.07 (0.05, 0.11) | |

FIG. 6C

| MODEL | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|
| CUT-POINTS | BP_diff Mean < 0.1 | Yes vs. No | 4.86 | 1.83 | 12.89 | <0.01 | 5,439.86 | 5,224.25 |
| | DBT_diff Mean > -5 | Yes vs. No | 3.42 | 1.68 | 6.94 | <0.01 | | |

FIG. 7B

MODEL 1

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Mean > 0.1 | Yes vs. No | 4.86 (4.49, 5.28) | 1.82 (1.72, 1.97) | 12.97 (11.61, 14.57) | <0.01 (<0.01, <0.01) | 5,443.67 (4,964.56, 5,991.72) |
| | DBT_diff Mean < -5 | Yes vs. No | 3.43 (3.03, 3.93) | 1.68 (1.53, 1.86) | 7.01 (5.99, 8.35) | <0.01 (<0.01, <0.01) | |

MODEL 2

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Mean > 0.3 | Yes vs. No | 2.12 (2.01, 2.21) | 1.26 (1.22, 1.31) | 3.54 (3.32, 3.76) | <0.01 (<0.01, <0.01) | 6,104.47 (5,494.60, 6,823.08) |
| | DBT_diff Mean < -5 | Yes vs. No | 4.51 (3.91, 5.21) | 2.09 (1.82, 2.39) | 9.76 (8.42, 11.42) | <0.01 (<0.01, <0.01) | |

MODEL 3

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Mean > 0.3 | Yes vs. No | 3.47 (3.33, 3.63) | 2.11 (2.05, 2.18) | 5.71 (5.41, 6.05) | <0.01 (<0.01, <0.01) | 6,550.29 (5,911.80, 7,296.05) |
| | DBT_diff Mean < 0 | Yes vs. No | 3.88 (3.50, 4.27) | 1.43 (1.31, 1.56) | 10.50 (9.39, 11.77) | 0.01 (<0.01, 0.01) | |

FIG. 7C

| MODEL | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|
| CUT-POINT | BP 24hr Max ≤ -0.01 | Yes vs. No | 3.82 | 1.55 | 9.39 | <0.01 | 1939.50 | 1870.69 |

FIG. 8B

MODEL 1

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Max ≤ -0.01 | Yes vs. No | 3.82 (9.19, 4.62) | 1.54 (1.32, 1.77) | 9.52 (7.68, 12.12) | <0.01 (<0.01, 0.01) | 1,938.96 (1,674.04, 2,221.93) |

MODEL 2

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP_diff Max ≤ 0.00 | Yes vs. No | 5.85 (4.58, 7.59) | 1.97 (1.60, 2.39) | 17.37 (13.18, 24.09) | <0.01 (<0.01, <0.01) | 1,655.49 (1,422.38, 1,892.62) |

| MODEL | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|
| CUT-POINT | BP Daily Mean ≤ 29.44 | Yes vs. No | 3.52 | 1.53 | 8.12 | <0.01 | 1861.65 | 1,767.30 |
| | DBT Daily Mean ≤ 77 | Yes vs. No | 3.45 | 1.63 | 7.31 | <0.01 | | |

FIG. 9C

MODEL 1

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP Daily Mean ≤ 29.44 | Yes vs. No | 3.56 (2.98, 4.27) | 1.53 (1.30, 1.80) | 8.29 (6.85, 10.13) | <0.01 (0.01, 0.01) | 1,851.18 (1,466.10, 2,259.09) |
| | DBT Daily Mean ≤ 77 | Yes vs. No | 3.44 (3.07, 3.83) | 1.61 (1.38, 1.81) | 7.36 (6.74, 8.12) | <0.01 (<0.01, 0.01) | |

MODEL 2

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | BP Daily Mean ≤ 29.42 | Yes vs. No | 3.58 (2.96, 4.35) | 1.61 (1.34, 1.93) | 7.96 (6.50, 9.97) | <0.01 (<0.01, 0.01) | 1,844.94 (1,449.66, 2,254.61) |
| | DBT Daily Mean ≤ 77 | Yes vs. No | 3.15 (2.76, 3.54) | 1.44 (1.23, 1.63) | 6.89 (6.25, 7.69) | <0.01 (<0.01, 0.01) | |

| MODEL | PARAMETER | VARIABLE | RR | LOWER 95% CI | UPPER 95% CI | P-VALUE | QIC FIT STATISTIC | QICu FIT STATISTIC |
|---|---|---|---|---|---|---|---|---|
| CUT-POINT | RH 24hr Mean ≥ 7 | Yes vs. No | 3.27 | 1.73 | 6.19 | <0.01 | 2,569.87 | 2,431.07 |

FIG. 10B

MODEL 1

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | RH diff Mean ≥ 7 | Yes vs. No | 3.27 (3.13, 3.41) | 1.72 (1.66, 1.78) | 6.22 (5.87, 6.60) | <0.01 (<0.01, <0.01) | 2,564.84 (2,330.54, 2,787.93) |

MODEL 2

| MODEL | PARAMETER | VARIABLE | RR | LOWER 95% CI | UPPER 95% CI | P-VALUE | QIC FIT STATISTIC |
|---|---|---|---|---|---|---|---|
| CUT-POINTS | RH diff Mean ≥ 5 | Yes vs. No | 3.12 (2.96, 3.28) | 1.64 (1.56, 1.71) | 5.94 (5.61, 6.34) | <0.01 (<0.01, <0.01) | 2,577.62 (2,339.41, 2,802.93) |

FIG. 10C

METHODS FOR DETERMINING RISK AND TREATING DISEASES AND CONDITIONS THAT CORRELATE TO WEATHER DATA

PRIORITY CLAIM

This application claims priority under 35 U.S.C. § 119 to U.S. Provisional No. 62/046,681 filed Sep. 5, 2014, the entire disclosure of which is incorporated herein.

TECHNICAL FIELD

The present invention relates generally to methods, products and models of risk management for experiencing adverse weather-associated symptoms of medical conditions and diseases.

BACKGROUND

Although as many as 80% of patients who suffer from migraine headaches implicate "weather" as a trigger for migraine episodes, the evidence based on clinical experience and epidemiologic studies is mixed. Not all patients are equally as perceptive of weather parameters and not all patients report the same weather factors as a trigger. Researchers have attempted for years to more clearly delineate weather's role in predicting migraine headache onset, typically evaluating individual meteorologic "weather" factors (e.g., barometric pressure, temperature, humidity, wind) as heterogeneous, continuous predictors of migraine. To date, none have developed a model with a high degree of predictive value, and some researchers have disparaged the concept due to apparent inconsistency in the data.

For example, one study reported that low barometric pressure during the preceding two days was associated with a higher frequency of emergency room visits for severe headache while others found the opposite or no relationship. Temperature has also shown mixed results; high temperature in the preceding 24 hours has been found to increase emergency room visits for severe headache by 7.5% for every 5 degree increase in temperature, but other studies have found no effect of temperature on migraine onset or severity.

Self-help internet sites (e.g., accuweather.com, weather.com) produce daily "migraine" risk models. However, the methodological development is not apparently published or corroborated by any reports of predictive accuracy. These models tend to collapse migraine risk across regions of the country, which could be problematic as one cannot assume the transportability of models from one location to another. The challenge of this and other models is that they can potentially do more harm than good. When the predicted high-risk event fails to materialize (as is often the case), patients become immune to future risk warnings and are thus unprepared when an actual event occurs. Alternatively, lumping large areas of the country under a similar risk level makes the individual less likely to personalize the information.

Another key problem with existing models is lack of scalability. Models generated from population data across varied climate regions, models generated from population data across a single climate region, and models generated from individual data in a single geographic area are not equivalent predictors at the level of an individual.

A migraine early warning system would afford patients an invaluable tool to help them take steps to ward off and/or be prepared to combat a potential attack. Current models that tout a "migraine risk" predictor have limited specificity and, as such, limited utility given their high false positive predictive rates.

Although migraine may be seen as the prototypical episodic disease event given its propensity for being susceptible to changing weather conditions, other diseases and health conditions also exhibit weather dependency. For example, asthma, emphysema (COPD), depression, anxiety, osteoarthritis, fibromyalgia and stroke are all reported in the literature as having a weather-based component to onset, flare-ups and severity.

Conceptual and methodological barriers have impeded efforts to construct a reliable model for prediction of weather-based risk. First, most researchers and patients have considered weather parameters as independent factors rather than evaluating them concurrently and consecutively. Second, most have failed to consider how meteorological changes may be especially predictive of weather-triggered health events. Third, many have only considered linear-based risk. Fourth, researchers often fail to fully account for seasonal weather variations within and across different climate regions. Finally, few have linked reoccurring weather patterns to migraine risk. Clearly, there remains a need in the art for valid, reliable models for predicting risk of weather-associated diseases and medical conditions both for populations and at the level of the individual.

SUMMARY

Accordingly, the present investigators combined clinical, analytical, and technologic expertise from meteorology, headache medicine, and bioinformatics to develop predictive weather-based medical condition risk models, illustrated by detailed guidance in the development of weather-based migraine headache risk-predictive models. Key innovations include: 1) considering composite weather measures of both the absolute, central tendencies (mean, median), and differentials (i.e., changes in weather measures over varying time intervals); 2) evaluating the heterogeneity and interdependency of weather conditions via advanced statistical modeling; 3) producing dynamic season specific models; and 4) creating a customizable tiered migraine risk model.

The inventive methods are not limited to predicting migraine and may be applied to generate predictive models for any weather-associated disease or condition, including, for example, hospital admission and readmission rates. The methods and models are scalable to the level of an individual or to population studies, and are customizable across climate regions and across seasons within climate regions, and are fully customizable to reflect unique weather-associated triggers of a given patient. The features of accounting for the interdependency of weather measurements, evaluating varying weather observations and change at varying intervals, allowing for non-linear seasonal variations, acquiring average weather conditions over a defined geographic area, and creating customizable tiered risk models, when combined, can be applied to a host of disease entities.

One embodiment of the invention provides methods for generating model sets of equations for predicting a risk of a subject who experiences adverse medical events associated with the weather, of experiencing a new-onset event (NOE). The methods comprise: a) identifying a climate region of interest; b) collecting daily mean barometric pressure (BP) data for a time frame and dividing the days of the time frame into at least upper, middle and lower quantile BP days to identify the upper quantile BP days; c) collecting daily NOE data for a subject cohort consisting of subjects known to suffer from the adverse medical event for the time frame and calculating a daily incident rate (IR) of NOEs for each day of the time frame and dividing the days of the time frame into at least upper, middle and lower quantile IR-NOE days to identify the upper quantile IR-NOE (UQ-IR-NOE) days; d) determining a relevant number of seasons based on an association between the upper IR-NOE quantile days identified in c) and the upper BP quantile days identified in b); e) collecting hourly weather data for the time frame for a number of weather parameters and determining a set of weather variables; f) employing a generalized linear regression analysis to generate a rank for each weather variable as a predictor of the UQ-IR-NOE days for each relevant season, for each BP quantile; g) identifying a risk-predictive equation using a forward stepwise approach.

The generated model comprises a set of one or more equations for predicting the risk of a subject experiencing a new-onset event (NOE) at the completion of step g. Different climate regions and different medical conditions may involve a different number of relevant seasons. In specific embodiments, regression analysis of the UQ-BP days and the UQ-IR-NOE days across a time frame (for example, one year) may be used to determine a number of relevant seasons. For example, for patients suffering from migraine headaches, which are known to be weather-associated, and residing in the Koppen-Geiger climate region Cfa, the regression analysis revealed two relevant seasons, referred to in very specific embodiments disclosed herein as F/W/S and Summer.

According to some embodiments, model equations may be used to predict a risk of a patient suffering from a new onset event on a future day. In specific embodiments, a risk-predictive model set of equations is generated for patients suffering from migraine headaches and residing in climate region Cfa:

[season=$F/W/S$,BP tertile=lower]$R=e^{[\beta_0+\beta_1 A+\beta_2 B]}+N+\varepsilon$ or $1=e^{[\beta_0+\beta_1 A+\beta_2 A(exp)2+\beta_3 B+\beta_4 B(exp)2]}+N+\varepsilon$   1.

[season=$F/W/S$,BP tertile=middle]$R=e^{[\beta_0+\beta_1 A+\beta_2 B]}+N+\varepsilon$   2.

[season=$F/W/S$,BP tertile=upper]$R=e^{[\beta_0+\beta_1 A+\beta_2 C]}+N+\varepsilon$   3.

[season=Summer,BP tertile=lower]$R=e^{[\beta_0+\beta_1 E]}+N+\varepsilon$   4.

[season=Summer,BP tertile=middle]$R=e^{[\beta_0+\beta_1 G+\beta_2 F]}+N+\varepsilon$   5.

[season=Summer,BP tertile=upper]$R=e^{[\beta_0+\beta_1 H]}+N+\varepsilon$   6.

wherein R is the risk, N is the number of subjects in the cohort eligible to have a new onset headache (NOH) on a given day and is the denominator in the IR-NOH calculation, and $\varepsilon$ is an error term of GEE regression modeling.

Other weather-implicated diseases and/or medical conditions susceptible to risk-predictive modeling according to embodiments of the invention include, but are not limited to, asthma, emphysema, depression, cardiovascular disease, arthritis, artherosclerosis, and diabetes.

According to specific embodiments, once a risk-predictive model is generated according to the invention, the subject may predict a risk of experiencing a new onset event on a future day by identifying an appropriate model equation based on the subject's residential climate region, the season, and the predicted BP on the future day, and then entering the predicted weather data called for by the appropriate equation.

A further embodiment provides methods for increasing efficiency in a hospital staffing and resource commitment by predicting high admission days, a "high" admission day being defined as a day falling in an upper quantile of the hospital's daily admissions for a year. The methods comprise: 1) generating a model set of equations for predicting a risk of subjects who suffer from weather-implicated medical conditions of being admitted to the hospital, wherein "generating" comprises the steps of: a) identifying the climate region in which the hospital is located; b) collecting daily mean barometric pressure (BP) data for the year and dividing the mean BP data into upper, lower and middle quantiles; c) collecting daily hospital admissions data for a subject cohort for the year, said subject cohort consisting of subjects known to suffer from a weather-implicated medical condition and who have been admitted to a hospital at least once previously due to experiencing an adverse event associated with the condition, to calculate a daily admission rate (AR) for each day of the year and to determine an upper quantile of days associated with the AR; d) determining a number of relevant seasons based on regression analysis of the upper BP quantile days and the upper AR quantile days; e) collecting weather parameter data across the year; f) employing GEE modeling to generate a rank for each weather variable as a continuous predictor of the upper quantile AR days for each relevant season, for each BP quantile; g) identifying a best predictive single variable equation based on p-value and QIC fit of the first-ranked weather variable in each relevant season, for each BP quantile; h) adding the next-ranked weather variable to the identified equation from g) in each season, for each BP and determining if fit improves; and i) repeating step h) until addition of the next-ranked weather variable fails to improve fit, wherein the model comprises a set of equations for predicting a risk of subjects who suffer from weather-implicated medical conditions of being admitted to the hospital at the completion of step i); 2) employing the model to determine which days are likely to be upper quantile admission rate (UQ-AR) days; and 3) staffing the hospital and committing resources to the hospital on the basis of the determination in step 2).

Embodiments are also directed to articles of manufacture comprising computer-readable code for implementing methods for predicting risk of experiencing a new onset symptom such as a migraine headache in accordance with embodiments of the invention. In specific embodiments the article comprises a mobile application software product.

These and other embodiments and aspects of the invention we be further clarified and understood by reference to the Figures and Detailed Description herein.

DETAILED DESCRIPTION

Highly reliable weather based models for predicting risk of experiencing a new-onset symptom of a weather-associated disease or condition are detailed herein. The inventive models are characterized by their dynamic nature and scalability by leveraging the heterogeneity of weather factors.

Models generated in accordance with aspects of the invention are contemplated as climate region-specific, although derivation of a model is similar regardless of climate and there may be between-climate region overlap. Any climate classification scheme is suitable so long as model-generation data is derived from the same classified climate region as the residence of a subject or from the climate region of the area under risk assessment. According to specific embodiments of the invention the risk-predictive models are generated for climate regions classified under the Koppen climate classification scheme, which divides climates into five main groups (A, B, C, D, E), each having several types and subtypes. Each particular climate type is represented by a two- to four-letter symbol. The Koppen climate classification is based on the empirical relationship between climate and vegetation and provides an efficient way to describe climatic conditions defined by temperature and precipitation and their seasonality with a single metric. The present investigators discovered that the seasonal variation (or lack thereof) within a climate region impacts a predictive model for residents of the climate region. The five main Köppen groups include:

GROUP A: Tropical/megathermal climates—characterized by constant high temperatures (at sea level and low elevations) across the year and includes tropical rainforest (Af) tropical monsoon (Am) and tropical savanna (Aw, As).

GROUP B: Dry (arid and semiarid) climates; characterized by actual precipitation less than a threshold value set equal to the potential evapotranspiration, and includes desert (BWh, BWk), and semi-arid (BSh, BSk).

GROUP C: Temperate/mesothermal climates; characterized by an average monthly temperature above 10° C. (50° F.) in their warmest months, and an average monthly temperature above −3° C. (27° F.) in their coldest months, and includes humid subtropical (Cfa, Cwa), oceanic (Cfb, Cwb, Cfc, Cwc), and Mediterranean (Csa, Csb).

GROUP D: Continental/microthermal climates; characterized by an average temperature above 10° C. (50° F.) in their warmest months, and a coldest month average below −3° C. (or 0° C. in some versions, as noted previously), and includes humid continental (Dfa, Dwa, Dfb, Dwb, Dsa, Dsb), and subarctic (Dfc, Dwc, Dfd, Dwd, Dsc, Dsd).

GROUP E: Polar and Alpine climates; characterized by average temperatures below 10° C. in all 12 months of the year, and includes tundra (ET), ice cap (EF), and alpine (ET, EF).

GROUP H: climates that are strongly influenced by the effects of altitude. As a result, the climate of such locations is different from places with low elevations at similar latitudes.

Figure 11:
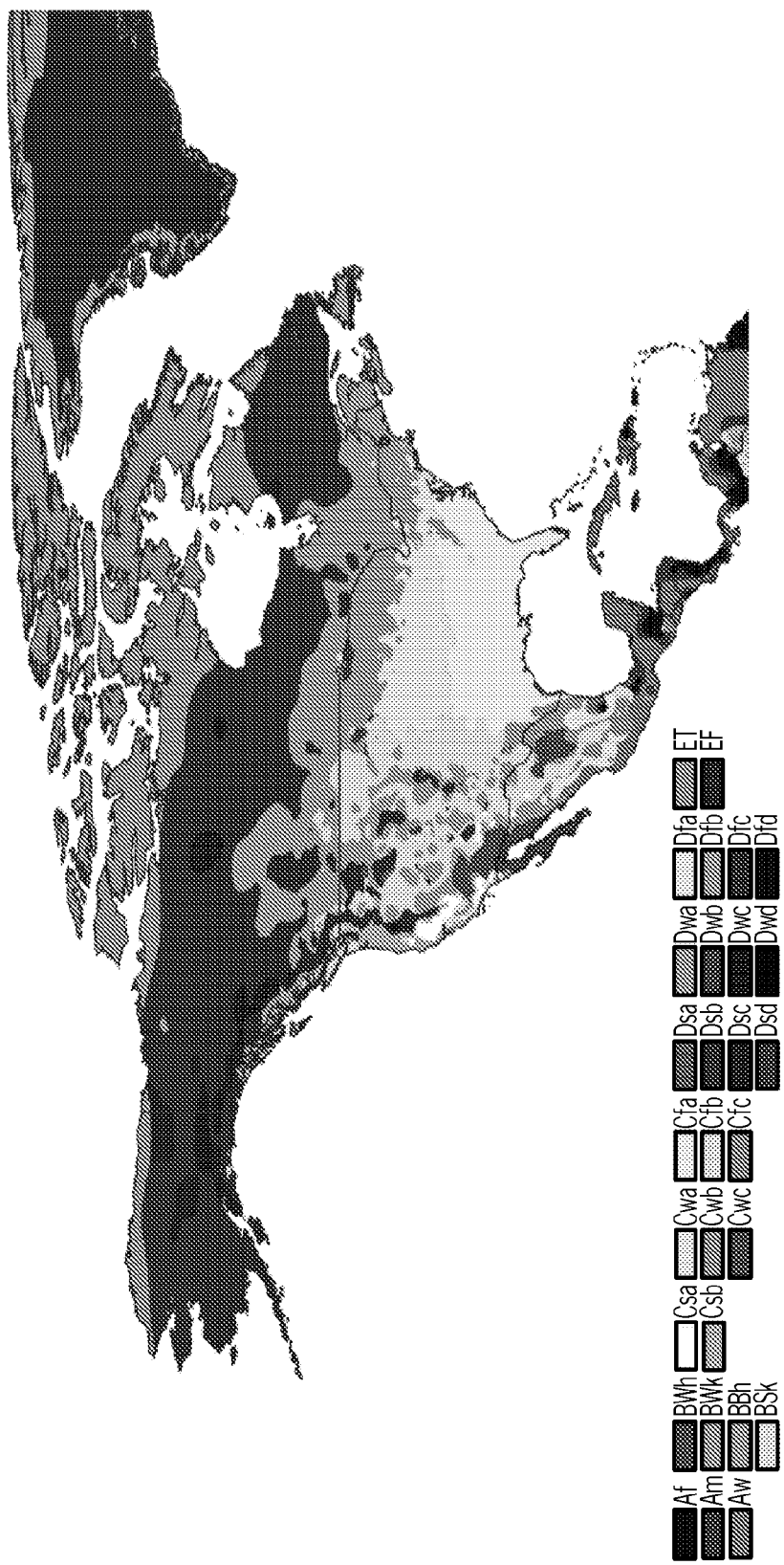
FIG. 11. A Koppen climate classification map and key for North America

The Koppen classification scheme applied to North America is set forth as FIG. 11, with attribution to A Peel, M. C. and Finlayson, B. L. and McMahon, T. A. (2007). "Updated world map of the Köppen-Geiger climate classification". Hydrol. Earth Syst. Sci. 11: 1633-1644. doi: 10.5194/hess-11-1633-2007, the entire disclosure of which is incorporated herein by this reference.

Particular embodiments of the invention provide methods for generating model sets of equations for predicting a risk of a subject who experiences adverse medical events associated with the weather, of experiencing a new-onset event (NOE). The methods comprise: a) identifying a climate region of interest; b) collecting daily mean barometric pressure (BP) data for a time frame and dividing the days of the time frame into at least upper, middle and lower quantile BP days to identify the upper quantile BP days; c) collecting daily NOE data for a subject cohort consisting of subjects known to suffer from the adverse medical event for the time frame and calculating a daily incident rate (IR) of NOEs for each day of the time frame and dividing the days of the time frame into at least upper, middle and lower quantile IR-NOE days to identify the upper quantile IR-NOE (UQ-IR-NOE) days; d) determining a relevant number of seasons based on an association between the upper IR-NOE quantile days identified in c) and the upper BP quantile days identified in b); e) collecting hourly weather data for the time frame for a number of weather parameters and determining a set of weather variables; f) employing a generalized linear regression analysis to generate a rank for each weather variable as a predictor of the UQ-IR-NOE days for each relevant season, for each BP quantile; g) identifying a risk-predictive equation using a forward stepwise approach. According to specific embodiments, the number of relevant seasons is 1, 2, 3 or 4 and the time frame is a time frame encompassing at least a portion of each relevant season. In more specific embodiments the time frame is for one year. The term "year" herein may include a number of days approximating one year. In specific embodiments one year is between 300 and 400 days, between 320 and 380 days, between 340 and 370 days, or 365 days±5 days.

According to specific embodiments, the generalized linear regression analysis comprises a generalized linear mixed model (GLMM) analysis (see Jiang, J. (2007), Linear and Generalized Linear Mixed Models and Their Applications, Springer, the entire disclosure of which is incorporated herein by this reference). According to other embodiments the generalized linear regression analysis comprises a generalized estimating equation (GEE) analysis (see, e.g. Hardin, James; Hilbe, Joseph (2003). Generalized Estimating Equations. London: Chapman and Hall/CRC, the entire disclosure of which is incorporated herein by this reference). Software for solving generalized estimating equations is available in MATLAB, SAS (proc genmod), SPSS (the gee procedure), Stata (the xtgee command) and R (packages gee, geepack and multgee). In certain aspects a generalized linear regression analysis is used to generate a rank for each weather variable as a continuous predictor of the UQ-IR-NOE days for each relevant season.

In specific embodiments, the generalized linear regression analysis step comprises GEE and the forward stepwise approach of step (g) comprises the following steps: i) identifying a best predictive single variable equation based on p-value and quasi-likelihood independence criterion (QIC) fit of the first-ranked weather variable in each season, for each BP quantile; ii) adding the next-ranked weather variable to the identified equation from g) in each season, for each BP and determine if fit improves; and iii) repeating step (ii) until addition of the next-ranked weather variable to the model fails to improve fit. In other specific embodiments the generalized linear regression analysis comprises a generalized mixed regression analysis and the forward stepwise approach of step (g) comprises the following steps: i) identifying a best predictive single variable equation based on Akaike information criterion (AIC) fit of the first-ranked variable in each season, for each BP quantile; ii) adding the next-ranked weather variable to the identified equation from (g) in each season, for each BP and determine if fit improves; and iii) repeating step (ii) until addition of the next-ranked variable to the model fails to improve fit.

The number of relevant seasons may be determined based on a regression analysis of the UQ-BP and the UQ-IR-NOE. The regression analysis comprises one or both of leverage point diagnostics and outlier detection diagnostics. After fitting a regression model, diagnostics are used to determine whether all the necessary model assumptions are valid. Relevant seasons are defined as periods of the year in which different model equations are valid.

Daily incident rate is equal to the number of subjects experiencing an NOE divided by the total number of eligible subjects. In specific embodiments, an "eligible subject" is defined as a subject who has not experienced an event in the preceding 24 hours. An "event" in this context is measured from the onset of a symptom until the subject returns to a normal, pre-symptom state. For example, where an event is experiencing a migraine headache, an eligible subject has not experienced a headache in the last 24 hours, regardless of the time of onset of the last-experienced headache. In another specific example, where an event is experiencing an outbreak of psoriasis, an eligible subject has been completely clear of psoriasis for the last 24 hours. According to yet another specific example, where an event is experiencing arthritic joint pain, an eligible subject did not experience joint pain in the last 24 hours.

In specific embodiments, the subject cohort is further controlled according to factors known to influence frequency of a medical condition underpinning an adverse event associated with the weather. For example, the cohort may be controlled for race, gender, age, socio-economic status, co-morbidities, tobacco use, alcohol use and general health of the subject, which may further increase the predictive reliability of the model for some subjects.

Weather variables in accordance with aspects of the invention are based on weather parameters including but not limited to barometric pressure (BP), wind speed (WS), wind direction (WD), dry bulb temperature (DBT), lightening activity (LA), relative humidity (RH), and precipitation (P). Weather variables may comprise daily mean and multiple differential maximums, minimums and means for each selected parameter. Multiple differentials are selected from a 24 hour differential, a 12 hour differential, a 6 hour differential a 3 hour differential, and combinations thereof for each selected parameter. Weather parameter data according to specific aspects may be gathered by looking up data for historical time periods or by looking up forecast data for future time frames. Databases include, for example, Climate Data Online at https://www.ncdc.noaa.gov/cdo-web/, and the National Weather Service Forecast data http://www-.weather.gov/forecastmap.

As noted above, the Köppen climate classification system divides the earth into six main climate regions designated by capital letters A, B, C, D, E and H, and over 20 sub-regions. Risk-predictive models according to embodiments of the invention are climate-region specific. Preferably, in generating a model, data is collected from multiple locations across a selected region or sub-region, and integrated. Example 1 illustrates data collection from five locations in Köppen climate sub-region Cfa. The regression analysis of the UQ-NOE and UQ-BP data collected in this region revealed two relevant seasons (validity of a model as assessed by model diagnostics exists within a relevant season). The relevant seasons for climate region Cfa are referred to herein as F/W/S corresponding to the time frame of from the fall equinox to the summer solstice, e.g. 9/21-6/20, and Summer, corresponding to the time frame of the summer solstice to the Fall equinox, e.g. 6/21-9/20).

According to very specific embodiments, the weather associated adverse event is experiencing a new onset of a migraine headache (NOE=NOH), the quantile is a tertile and the model set of equations includes the following determined weather variables: A) BP 24 hour differential mean; B) WS 24 hour differential maximum; C) DBT 24 hour differential mean; D) DBT 6 hour differential mean; E) BP 24 hour differential maximum; F) DBT daily mean; G) BP daily mean; and H) RH 24 hour differential mean. Other applicable quantiles include quartiles, quintiles, sextiles, deciles, and percentiles. The upper, middle and lower quantiles having more ranking divisions than tertiles are defined as any grouping that contains the uppermost quantile, any grouping that contains the middle-most quantile, and any grouping that contains the lower-most quantile, respectively.

A specific and non-limiting example of a risk predictive model set of equations generated according to the guidance provided in the Examples and specific to the Cfa climate region, where R=risk of a given day being a UT-IR-NOH day, comprises:

$$[\text{season}=F/W/S, BP \text{ tertile}=\text{lower}]R = e^{[\beta_0 + \beta_1 A + \beta_2 B]} + N + \varepsilon \text{ or } 1 = e^{[\beta_0 + \beta_1 A + \beta_2 A(exp)2 + \beta_3 B + \beta_4 B(exp)2]} + N + \varepsilon \quad 1.$$

$$[\text{season}=F/W/S, BP \text{ tertile}=\text{middle}]R = e^{[\beta_0 + \beta_1 A + \beta_2 B]} + N + \varepsilon \quad 2.$$

$$[\text{season}=F/W/S, BP\text{ tertile=upper}]R=e^{[\beta_0+\beta_1 A+\beta_2 C]}+N+\varepsilon \quad\quad 3.$$

$$[\text{season}=\text{Summer}, BP\text{ tertile=lower}]R=e^{[\beta_0+\beta_1 E]}+N+\varepsilon \quad\quad 4.$$

$$[\text{season}=\text{Summer}, BP\text{ tertile=middle}]$$
$$R=e^{[\beta_0+\beta_1 G+\beta_2 F]}+N+\varepsilon \quad\quad 5.$$

$$[\text{season}=\text{Summer}, BP\text{ tertile=upper}]R=e^{[\beta_0+\beta_1 H]}+N+\varepsilon \quad\quad 6.$$

wherein N is the number of subjects in the cohort eligible to have an NOH on a given day and is the denominator in the IR-NOH calculation, and $\varepsilon$ is an error term of GEE regression modeling. Weather variables are symbolized by the capital letter designations of the preceding paragraph for clarity.

Particular embodiments of methods of the invention are applicable at the level of an individual. A risk-predictive model is generated for a climate region, then subjects who experience weather-associated adverse events and who are residents of or visitors to the climate region may utilize the model to assess personal risk of experiencing a new onset adverse event on a given day, either present or future. According to one embodiment, the method comprises a) determining a climate region associated with the geographical location of the subject on the given day; b) determining the relevant season in which the given day falls; c) determining the projected mean BP for the day and identifying the given day as an upper, middle or lower quantile BP day; d) selecting an equation from a risk-predictive model set of equations generated for the determined climate region, determined relevant season and determined BP quantile; and e) entering weather variable data forecast for the given day into the selected equation to yield an assessment of the risk. The subject may then undertake treatment to avoid or mitigate the adverse event. In specific embodiments, the weather-implicated adverse event is associated with a condition selected from migraine headache, asthma, emphysema, depression, cardiovascular disease, arthritis, artherosclerosis, psoriasis and diabetes. In very specific embodiments, the adverse event is associated with artherosclerosis and comprises heart attack or stroke. In other very specific embodiments the adverse event is associated with arthritis and is joint pain. In other very specific embodiments the adverse event is associated with migraine headaches and comprises experiencing a new onset migraine headache.

In accordance with specific method embodiments where the adverse event is experiencing a new onset migraine headache and the subject resides in climate region Cfa, the method comprises: a) determining the relevant season in which the given day falls; b) determining whether the given day is an upper, middle or lower BP tertile day; c) selecting an equation from the model set of equations according to claim 16 specific to the determined relevant season and the determined BP tertile; d) entering weather variable data for the given day into the selected equation to yield an assessment of the risk.

Ultimately, when scaled to the individual subject, embodiments of the risk-predictive models are intended to provide enhanced symptom management and mitigating/preventative treatment benefits to a subject who suffers from a weather-associated medical condition or disease. For example, if a subject known to suffer from weather-associated migraine headaches utilizes an inventive model to determine that a greater-than-not risk exists tomorrow for experiencing a new onset migraine headache, the subject may undertake preventative or mitigating treatment at a point where such treatment is most effective—prior to onset of clinical symptoms. It is contemplated therefore that embodiments of the inventive models may be incorporated into individual treatment regimens by clinicians.

Non-limiting examples of migraine headache preventative interventions and treatments which may be undertaken upon determination of a greater-than-not risk include: cardiovascular drugs such as the beta blockers exemplified by triptans exemplified by frovatriptan (Frova), sumatriptan (Imitrex), rizatriptan (Maxalt), zolmitriptan (Zomig), almotriptan (Axert), electriptan (Relpax), naratriptan (Amerge); propranolol (Inderal La, Innopran XL, others), metoprolol tartrate (Lopressor) and timolol (Betimol); calcium channel blockers exemplified by Verapamil (Calan, Verelan, others); angiotensin-converting enzyme inhibitors exemplified by lisinopril (Zestril); antidepressants such as the tricyclic antidepressants exemplified by Amitriptyline, and serotonin and norepinephrine reuptake inhibitors exemplified by venlafaxine (Effexor XR); anti-seizure drugs exemplified by valproate sodium (Depacon) and topiramate (Topamax); and pain relievers such as nonsteroidal anti-inflammatory drugs exemplified by naproxen (Naprosyn).

According to some embodiments, weather predictive risk models may be utilized to predict hospital admissions/readmissions. The models may identify high risk days for hospital admissions for common weather-associated disorders including, for example, asthma, emphysema, depression, heart attack, and stroke. Preventative medical treatments may be optimized on high risk days to decrease admission and rate of readmission to hospitals/clinics. Staffing and resource commitment may be allocated according to high versus low risk days based on the model.

Readmission is a major problem for U.S. health care efficiency. Eighteen percent of all Medicare patients are readmitted to the hospital within one month of release. In the context of Medicare, admissions carry steep penalties and the cost to the US economy is estimated to be 26 billion dollars, of which approximately 17 billion is preventable. Currently, care management programs constitute a thriving medical side industry aimed at reducing these numbers.

One embodiment is directed to methods for increasing efficiency in hospital staffing and resource commitment by predicting high admission days, a "high" admission day being defined as a day falling in an upper quantile of the hospital's daily admissions for a year. According to one specific embodiment the method comprises: generating a model set of equations for predicting a risk of subjects who suffer from weather-associated medical conditions of being admitted to the hospital, wherein "generating" comprises the steps of: identifying the climate region in which the hospital is located; collecting daily mean barometric pressure (BP) data for the year and dividing the mean BP data into upper, lower and middle quantiles; collecting daily hospital admissions data for a subject cohort for the year, said subject cohort consisting of subjects known to suffer from a weather-associated medical condition and who have been admitted to a hospital at least once previously due to experiencing an adverse event associated with the condition, to calculate a daily admission rate (AR) for each day of the year and to determine an upper quantile of days associated with the AR; determining a number of relevant seasons based on regression analysis of the upper BP quantile days and the upper AR quantile days; collecting weather parameter data across the year; employing GEE modeling to generate a rank for each weather variable as a continuous predictor of the upper quantile AR days for each relevant season, for each BP quantile; identifying a best predictive single variable equation based on p-value and QIC fit of the first-ranked weather variable in each relevant season, for each BP quantile; adding the next-ranked weather variable to the identified equation from g) in each season, for each BP and determining if fit improves; repeating step h) until addition of the next-ranked weather variable fails to improve fit, wherein the model comprises a set of equations for predicting a risk of subjects who suffer from weather-associated medical conditions of being admitted to the hospital at the completion of step i); employing the model to determine which days are likely to be upper quantile admission rate (UQ-AR) days; and staffing the hospital and committing resources to the hospital on the basis of the determination in step 2).

According to another specific embodiment, an article of manufacture comprising computer readable code for implementing methods according to the invention is provided. A very specific embodiment comprises mobile application weather-based risk prediction software for implementing the methods of the invention by a mobile device such as a smart phone, tablet, smart watch and the like, enabling real-time risk prediction to subjects who suffer from weather-implicated conditions. Response to the risk may be proactive and designed to manage the risk. For example, medications and treatments are available that are effective in mitigating the severity or preventing onset of symptoms of many weather-implicated diseases and conditions, including migraine headaches. The software may be customizable by a patient according to geographical area of residence and patient-specific historical data. For example, in creating a risk predictive model, the patient's medical history may be utilized to generate a model set of equations across any time frame desired. In other specific embodiments the software responds to user input by adapting the risk-predictive model to actual outcomes.

According to specific embodiments, including personalized mobile application embodiments, an initial query is to identify whether the disease or condition of a given patient is weather-associated with respect to the individual patient. For example, the patient may be requested to keep a symptom log for a period of time ranging from about 30 to about 60, 90, 120 or 180 days. The patient's individual incidence rate is correlated to the weather data across the same period of time for weather variables found to be significant at a population level for the particular disease or condition, and the set of weather variables/differentials significant to predicting risk in the individual patient is determined. With enough data specific cut-points for the weather variables may also be determined at the level of the individual and model equations predictive at the level of an individual patient may be ascertained. Embodiments are contemplated whereby the programmed model equations may be utilized by the patient to predict risk of experiencing a symptom associated with the disease or condition on a future day utilizing weather data forecast databases to calculate estimated risk. Degree of risk may also be a programmable output. Such databases are provided, for example, by the U.S. National Weather Service at http://www.weather.gov/forecastmap. Based on the individual's patients needs, prophylactic treatment may be undertaken or a schedule may be adjusted in response to the calculated risk.

EXAMPLES

The following examples are set forth to illustrate particular aspects and features of the invention and should not be construed as limiting the full scope of the invention as defined by the claims.

Example 1

The following example illustrates derivation of a risk-predictive model set of equations applicable to residents of climate region Cfa. Therefore, the stated seasons correspond to the following dates: Summer—6/21 to 9/20; Fall—9/21 to 12/20; Winter—12/21 to 3/20; Spring—3/21 to 6/20. As detailed below, it was determined that for the Cfa climate region, there are two model-relevant seasons: F/W/S corresponding to the dates of 9/21 to 6/20; and Summer corresponding to the dates of 6/21 to 9/20.

Illustrative inventive risk-predictive models were developed from headache data obtained from subjects suffering from migraine headaches residing in St. Louis, Mo. Each subject completed a daily headache diary for 2-6 months recording the presence or absence of headache. Therefore, multiple persons recorded headache data on the same days.

The primary outcome measure for the study was whether a specific day's incidence rate (IR) of new onset headache (NOH) was among the top third of daily IR-NOH during the season in which that day fell. Those days that did have daily IR-NOH rates among the top third for that season were considered to be in the upper tertile (UT) for that season (and were labeled "UT-IR-NOH"). NOH was defined as the presence of headache on a given day coupled with the absence of headache on the preceding day for an individual. Daily NOH incidence (IR-NOH) were then calculated. The daily IR-NOH numerator was the total number of individuals with NOH on a given day and the denominator was the total number of individuals eligible to have NOH on that same day. Subjects were excluded from the denominator if they had a headache the day before because by definition they could not have had a "new" headache that day. For example, if 25 subjects recorded on a given day, but five of them had a headache the day before then the daily IR-NOH only included data from 20 participants. Daily IR-NOH for each season was then calculated and the highest 33% of daily IR-NOH rates for that season were designated as being UT-IR-NOH.

A full suite of hourly weather data was obtained from the National Weather Service for five different weather stations located in the St. Louis area for each day of the study. The weather variables measured hourly included barometric pressure (BP), relative humidity (RH), dry bulb temperature (DBT), wind direction (WD), and wind speed (WS). The maximum, minimum, and mean values of these variables were recorded. The hourly weather measurements from the five weather stations were averaged to come up with average representative weather variables for a given day in the St. Louis metro area. 3, 6, 12, 24 and 48 hour weather differentials were also calculated based on these representative weather variables. A weather differential was defined as the value of the weather variable at time 0 minus that from a preceding time period (weather variable$_{Time\ 0}$−weather variable$_{PrecedingTime}$=weather differential).

The relative risks of a day being a UT-IR-NOH for that season were calculated using a Poisson regression model with a robust error variance. This methodology has been shown to be reliable in simulated and real data sets of various sizes and outcome incidence rates. The independent variables for these statistical models included the daily maximums, minimums and means of the weather variables at time 0 and other time intervals. The natural log of the number of subjects reporting their headache status on a given day was defined as the offset variable. The GEE model used an independent correlation structure, a subject effect of "day" representing each unique day in the analysis, and a within-subject effect of "ID" representing a unique identification number for every subject in the cohort.

Initial analysis suggested that BP was particularly important in determining which days were UT-IR-NOH. Moreover, it appeared that the days with the highest and lowest BP modeled different types of weather. Thus, prior to modeling daily UT-IR-NOH risk, daily mean BP distribution across each season was split into season specific categories; upper tertile, middle tertile, lower tertile. In addition, fall, winter and spring modeled similarly and were thus combined into one analysis. The summer season modeled differently from the other seasons and was modeled separately. A stratified analysis was performed on each seasonal group based upon mean BP tertiles. Therefore, there were a total of six stratified models (e.g. models of fall/winter/spring and summer for each of the three BP tertiles). In addition, alternative models of fall/winter/spring and all four seasons together that combined the low and middle tertiles of mean BP were also run.

In an effort to develop the optimal seasonal models, GEEs were employed to model each of the different weather variables as continuous predictors of UT-IR-NOH days. The p-values and quasi-likelihood under the independence model criterion (QIC) fit statistics for these models were obtained and the "best" single variable models were selected. The analysis was then repeated with the second most predictive weather variable being added to the model. If the second variable improved the fit of the model, then the "best" two variable models were selected and incorporated in a generalized additive model to identify potential cut-points for each variable. These variables were then entered in a second GEE model to determine the optimal models based upon QIC fit statistics. Some models included weather variables with specific cut points while others modeled the weather variable continuously.

Examples 2-7 set forth actual models that were found to be predictive for each of the stratified analyses. The weather variables used in the models are defined below:

1) BP 24 hour differential mean (BP_24hr_Diff_Mean) was calculated by subtracting the hourly BP from the preceding day (day −1) from that from the following day (Hourly $BP_{Day\ 0}$−Hourly $BP_{Day\ -1}$) at exactly the same time of each day. For example, the 1:00 AM BP from day −1 would be subtracted from the 1:00 AM BP on day 0. Therefore we obtained 24 differentials for a given day. The mean of these 24 hourly differentials was the BP_24hr_Diff_Mean for day 0.
2) WS 24 hour differential maximum (WS_24hr_Diff_Max) was calculated by subtracting the hourly WS from the preceding day (day −1) from that from the Hourly following day (Hourly $WS_{Day\ 0}$−$WS_{Day\ -1}$) at the same time. Therefore we obtained 24 differentials for a given day. The maximum of these 24 hourly differentials was the WS_24hr_Diff_Max for day 0.
3) DBT 24 hour differential mean (DBT_24hr_Diff_Mean) was calculated by subtracting the hourly DBTs from the preceding day (day −1) from that from the following day (Hourly $DBT_{Day\ 0}$−Hourly $DBT_{Day\ -1}$). Therefore we obtained 24 differentials for a given day. The mean of these 24 hourly differentials was the DBT_24hr_Diff_Mean for day 0.
4) DBT 6 hour differential mean (DBT_6hr_Diff_Mean) was calculated by subtracting the hourly DBT from 6 hours prior from that from that at a given hour during a day (Hourly $DBT_{Any\ hour\ during\ the\ day}$−Hourly $DBT_{6\ hours\ prior}$). For example, the hourly DBT from 3:00 AM was subtracted from the hourly DBT from 9:00 AM. Therefore, we obtained 24 six hour differentials for a given day. The mean of these 24 hourly differentials was the DBT_6hr_Diff_Mean for day 0.
5) BP 24 hour differential maximum (BP_24hr_Diff_Max) was calculated by subtracting the hourly BP from the preceding day (day −1) from that from the following day (Hourly $BP_{Day\ 0}$−Hourly $BP_{Day\ -1}$). Therefore we obtained 24 differentials for a given day. The maximum of these 24 hourly differentials was the BP_24hr_Diff_Max for day 0.
6) DBT daily mean (DBT_Daily_Mean) was defined as the mean of the 24 hourly measurements of DBT.
7) BP daily mean (BP_Daily_Mean) was defined as the mean of the 24 hourly measurements of BP.
8) RH 24 hour differential mean (RH_24hr_Diff_Mean) was calculated by subtracting the hourly humidity from the preceding day (day −1) from that from the following day (Hourly $RH_{Day\ 0}$−Hourly $RH_{Day\ -1}$). Therefore we obtained 24 differentials for a given day. The mean of these 24 hourly differentials was the RH_24hr_Diff_Mean for day 0.

Example 2

This example illustrates generation of four model equations for lower tertile BP days in the F/W/S season,
For the first, second and third model equations:
Outcome Variable: UT-IR-NOH
   1=Yes; the day is a UT-IR-NOH day for the season
   0=No; the day is not a UT-IR-NOH day for the season
   The intercept is represented by $\beta_0$
First Predictor Variable: BP_Diff_Mean_Low
   1=Yes; the day had a BP_24hr_Mean≤0.0
   0=No; the day did not have a BP_24hr_Diff_Mean≤0.0
   The coefficient for the predictor variable BP_Diff_Mean_Low is represented by $\beta_1$
Second predictor variable: WS_Diff_Max_ge_7
   1=Yes; the day had a WS_24hr_Diff_Max≥7
   0=No; the day did NOT have a WS_24hr_Diff_Max≥7
   The coefficient for the predictor variable WS_Diff_Max_ge_7 is represented by $\beta_2$
Offset term—variable log(N), where N=the number of patients eligible to have a NOH on the given day.
Error term of GEE regression model represented by "ε".
First Model Equation for lower BP tertile, F/W/S season: (estimated) $\hat{\beta}_0 = -6.2589$; $\hat{\beta}_1 = -6.2589$ and $\hat{\beta}_2 = 0.9731$.

| Model Information | |
|---|---|
| Data Set | WORK.FWS_LOW_BP_1 |
| Distribution | Poisson |
| Link Function | Log |
| Dependent Variable | Upper_Tertile_FWS |
| Offset Variable | LN_N |
| GEE Model Information | |
| Correlation Structure | Independent |
| Within-Subject Effect | ID (200 levels) |
| Subject Effect | Date (90 levels) |
| Number of Clusters | 90 |
| Correlation Matrix Dimension | 200 |
| Maximum Cluster Size | 99 |
| Minimum Cluster Size | 28 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −6.2589 | 0.4589 | −7.1583 | −5.3596 | −13.64 | <.0001 |
| BP_Diff_Mean_Low | 1 | 1.1736 | 0.4575 | 0.2770 | 2.0702 | 2.57 | 0.0103 |
| WS_Diff_Max_ge_7 | 1 | 0.9731 | 0.2846 | 0.4153 | 1.5309 | 3.42 | 0.0006 |

| Model | Parameter | Variable | RR | Lower 95% CI | Upper 95% CI | p-value |
|---|---|---|---|---|---|---|
| Cut-points | BP 24 hr_diff Mean ≤ 0.0 | Yes vs. No | 3.23 | 1.32 | 7.93 | 0.01 |
| | WS_24 hr diff Max ≥ 7 | Yes vs. No | 2.65 | 1.51 | 4.62 | <0.01 |

Log($UT\text{-}IR\text{-}NOH$ Day)=$\beta_0+\beta_1(BP\_Diff\_Mean\_Low)+\beta_2(WS\_Diff\_Max\_ge\_7)+\log(N)+\varepsilon$ First Model Equation:

Or equivalently, $UT\text{-}IR\text{-}NOH$ Day=$e^{[\beta_0+\beta_1(BP\_Diff\_Mean\_Low)+\beta_2(WS\_Diff\_Max\_ge\_7)]}+(N)+\varepsilon$ Second Model Equation for lower BP tertile, F/W/S season: (estimated) $\hat{\beta}_0=-6.1660$; $\hat{\beta}_1=1.2907$ and $\hat{\beta}_2=0.8440$.

| Model Information | |
|---|---|
| Data Set | WORK.FWS_LOW_BP_2 |
| Distribution | Poisson |
| Link Function | Log |
| Dependent Variable | Upper_Tertile_FWS |
| Offset Variable | LN_N |

| GEE Model Information | |
|---|---|
| Correlation Structure | Independent |
| Within-Subject Effect | ID (200 levels) |
| Subject Effect | Date (90 levels) |
| Number of Clusters | 90 |
| Correlation Matrix Dimension | 200 |
| Maximum Cluster Size | 99 |
| Minimum Cluster Size | 28 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −6.1660 | 0.4181 | −6.9854 | −5.3466 | −14.75 | <.0001 |
| BP_Diff_Mean_Low | 1 | 1.2907 | 0.3985 | 0.5097 | 2.0717 | 3.24 | 0.0012 |
| WS_Diff_Max_ge_7 | 1 | 0.8440 | 0.2815 | 0.2923 | 1.3958 | 3.00 | 0.0027 |

| Model | Parameter | Variable | RR | Lower 95% CI | Upper 95% CI | p-value |
|---|---|---|---|---|---|---|
| Cut-points | BP_24 hr diff Mean ≤ −0.05 | Yes vs. No | 3.64 | 1.66 | 7.94 | <0.01 |
| | WS_24 hr diff Max ≥ 7 | Yes vs. No | 2.33 | 1.34 | 4.04 | <0.01 |

Second Model Equation:
$$\log(\textit{UT-IR-NOH Day}) = \beta_0 + \beta_1(\textit{BP\_Diff\_Mean\_Low}) + \beta_2(\textit{WS\_Diff\_Max\_ge\_7}) + \log(N)$$

Or equivalently, $$\textit{UT-IR-NOH Day} = e^{[\beta_0 + \beta_1(\textit{BP\_Diff\_Mean\_Low}) + \beta_2(\textit{WS\_Diff\_Max\_ge\_7})] + (N) + \varepsilon}$$

Third Model Equation for lower BP tertile, F/W/S season: (estimated) $\hat{\beta}_0 = -5.8445$; $\hat{\beta}_1 = 1.1687$ and $\hat{\beta}_2 = 0.7252$

| Model Information | |
|---|---|
| Data Set | WORK.FWS_LOW_BP_3 |
| Distribution | Poisson |
| Link Function | Log |
| Dependent Variable | Upper_Tertile_FWS |
| Offset Variable | LN_N |

| GEE Model Information | |
|---|---|
| Correlation Structure | Independent |
| Within-Subject Effect | ID (200 levels) |
| Subject Effect | Date (90 levels) |
| Number of Clusters | 90 |
| Correlation Matrix Dimension | 200 |
| Maximum Cluster Size | 99 |
| Minimum Cluster Size | 28 |

Analysis Of GEE Parameter Estimates
Empirical Standard Error Estimates

| Parameter | | Estimate | Standard Error | 95% Confidence Limits | | Z | Pr > |Z| |
|---|---|---|---|---|---|---|---|
| Intercept | | −5.8445 | 0.3159 | −6.4637 | −5.2253 | −18.50 | <.0001 |
| BP_Diff_Mean_Low | 1 | 1.1687 | 0.3047 | 0.5715 | 1.7659 | 3.84 | 0.0001 |
| WS_Diff_Max_ge_7 | 1 | 0.7252 | 0.2726 | 0.1909 | 1.2594 | 2.66 | 0.0078 |

| Model | Parameter | Variable | RR | Lower 95% CI | Upper 95% CI | p-value |
|---|---|---|---|---|---|---|
| Cut-points | BP_24 hr diff Mean ≤ −0.10 | Yes vs. No | 3.22 | 1.77 | 5.85 | <0.01 |
| | WS_24 hr diff Max ≥ 7 | Yes vs. No | 2.07 | 1.21 | 3.52 | 0.01 |

Third Model Equation:
$$\log(\textit{UT-IR-NOH Day}) = \beta_0 + \beta_1(\textit{BP\_Diff\_Mean\_Low}) + \beta_2(\textit{WS\_Diff\_Max\_ge\_7}) + \log(N) + \varepsilon$$

Or equivalently, $$\textit{UT-IR-NOH Day} = e^{[\beta_0 + \beta_1(\textit{BP\_Diff\_Mean\_Low}) + \beta_2(\textit{WS\_Diff\_Max\_ge\_7})] + (N) + \varepsilon}$$

Fourth Model Equation for Lower BP Tertile, F/W/S Season:
For the Fourth Model Equation,
The intercept is represented by $\beta_0$ and is estimated such that $\hat{\beta}_0 = -6.5086$
First predictor variable is BP 24 hr diff Mean,
The coefficient for the first predictor variable is $\beta_1$ and is estimated such that $\hat{\beta}_1 = -4.4858$.

The second predictor variable is (BP 24 hr diff Mean)$^2$,
The coefficient for the second predictor variable is $\beta_2$ and is estimated such that $\hat{\beta}_2 = -2.1769$.
The third predictor variable is WS 24 hr diff Max
The coefficient for the third predictor variable is $\beta_3$ and is estimated such that $\hat{\beta}_3 = 0.2750$.
The fourth predictor variable is (WS 24 hr diff Max)$^2$.
The coefficient for the fourth predictor variable is $\beta_4$ and is estimated such that $\hat{\beta}_4 = 0.0111$.

The offset term is log(N), where N = the number of patients eligible to have a NOH on the given day. The error term of the regression model is represented by "$\varepsilon$".

| Model Information | |
|---|---|
| Data Set | WORK.FWS_LOW_BP_4 |
| Distribution | Poisson |
| Link Function | Log |
| Dependent Variable | Upper_Tertile_FWS |
| Offset Variable | LN_N |

-continued

| GEE Model Information | |
|---|---|
| Correlation Structure | Independent |
| Within-Subject Effect | ID (200 levels) |
| Subject Effect | Date (90 levels) |
| Number of Clusters | 90 |
| Correlation Matrix Dimension | 200 |
| Maximum Cluster Size | 99 |
| Minimum Cluster Size | 28 |

Analysis Of GEE Parameter Estimates
Empirical Standard Error Estimates

| Parameter | Estimate | Standard Error | 95% Confidence Limits | | Z | Pr > \|Z\| |
|---|---|---|---|---|---|---|
| Intercept | −6.5086 | 0.6736 | −7.8288 | −5.1884 | −9.66 | <.0001 |
| BP_24HR_DIFF_Mean | −4.4858 | 2.2688 | −8.9326 | −0.0391 | −1.98 | 0.0480 |
| BP_diff_mean_sq | −2.1769 | 5.8365 | −13.6162 | 9.2624 | −0.37 | 0.7092 |
| WS_24HR_DIFF_Maximum | 0.2750 | 0.1298 | 0.0206 | 0.5294 | 2.12 | 0.0341 |
| WS_diff_max_sq | −0.0111 | 0.0056 | −0.0222 | −0.0001 | −1.97 | 0.0486 |

| Parameter | Variable | RR | Lower 95% Cl | Upper 95% Cl | p-value |
|---|---|---|---|---|---|
| BP 24 hr diff Mean | 0.1 unit increase | 0.64 | 0.41 | 1.00 | 0.05 |
| (BP 24 hr diff Mean)$^2$ | 0.01 unit increase | 0.98 | 0.87 | 1.10 | 0.71 |
| WS 24 hr diff Max | 5 unit increase | 3.96 | 1.11 | 14.11 | 0.03 |
| (WS 24 hr diff Max)$^2$ | 25 unit increase | 0.76 | 0.57 | 1.00 | 0.05 |

$\log(UT\text{-}IR\text{-}NOH \text{ Day}) = \beta_0 + \beta_1(BP \text{ 24 hr diff Mean}) + \beta_2(BP \text{ 24 hr diff Mean})^2 + \beta_3(WS \text{ 24 hr diff Max}) + \beta_4(WS \text{ 24 hr diff Max})^2 + \log(N) +$ Fourth Model Equation:

Or equivalently, $UT\text{-}IR\text{-}NOH_2\text{Day} = e^{[\beta_0 + \beta_1(BP\ 24hr\ diff\ Mean) + \beta_2(BP\ 24hr\ diff\ Mean)^2 + \beta_3(WS\ 24hr\ diff\ Max) + \beta_4(WS\ 24hr\ diff\ Max)^2 + \log(N) + \varepsilon]} + (N) + \varepsilon$

Example 3

This example illustrates generation of model equations for middle tertile BP days in the F/W/S season. For the first and second model equations:

Outcome variable: UT-IR-NOH
  1=Yes; the day is a UT-IR-NOH day for the season
  0=No; the day is not a UT-IR-NOH day for the season
  The intercept is represented by $\beta_0$
First predictor variable: BP_Diff_Mean_Low
  1=Yes; the day had a BP_24hr_Diff_Mean≤0.0
  0=No; the day did not have a BP_24hr_Diff_Mean≤0.0
  The coefficient for the predictor variable BP_Diff_Mean_Low is represented by $\beta_1$
Second predictor variable: WS_Diff_Max_ge_6
  1=Yes; the day had a WS_24hr_Diff_Max≥6
  0=No; the day did NOT have a WS_24hr_Diff_Max≥6
  The coefficient for the predictor variable WS_Diff_Max_ge_7 is represented by $\beta_2$
Offset term—variable log(N), where N=the number of patients eligible to have a NOH on the given day.
Error term of GEE regression model represented by "$\varepsilon$".
First Model Equation for middle BP tertile in F/W/S season: $\hat{\beta}_0 = -6.3411$; $\hat{\beta}_1 = 0.7397$ and $\hat{\beta}_2 = 0.8112$.

| Model Information | |
|---|---|
| Data Set | WORK.FWS_AVG_BP_1 |
| Distribution | Poisson |
| Link Function | Log |
| Dependent Variable | Upper_Tertile_FWS |
| Offset Variable | LN_N |
| GEE Model Information | |
| Correlation Structure | Independent |
| Within-Subject Effect | ID (205 levels) |
| Subject Effect | Date (91 levels) |
| Number of Clusters | 91 |
| Correlation Matrix Dimension | 205 |
| Maximum Cluster Size | 92 |
| Minimum Cluster Size | 35 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −6.3411 | 0.5583 | −7.4353 | −5.2468 | −11.36 | <.0001 |
| BP_Diff_Mean_Low | 1 | 0.7397 | 0.4279 | −0.0990 | 1.5784 | 1.73 | 0.0839 |
| WS_Diff_Max_ge_6 | 1 | 0.8112 | 0.4513 | −0.0734 | 1.6957 | 1.80 | 0.0723 |

| Model | Parameter | Variable | RR | Lower 95% Cl | Upper 95% Cl | p-value |
|---|---|---|---|---|---|---|
| Cut-points | BP_24 hr diff Mean ≤ 0.0 | Yes vs. No | 2.10 | 0.91 | 4.85 | 0.08 |
| | WS_24 hr diff Max ≥ 6 | Yes vs. No | 2.25 | 0.93 | 5.45 | 0.07 |

$\log(UT\text{-}IR\text{-}NOH \text{ Day}) = \beta_0 + \beta_1(BP\_Diff\_Mean\_Low) + \beta_2(WS\_Diff\_Max\_ge\_6) + \log(N) + \varepsilon$ First Model Equation:

Or equivalently, $UT\text{-}IR\text{-}NOH \text{ Day} = e^{[\beta_0 + \beta_1(BP\_Diff\_Mean\_Low) + \beta_2(WS\_Diff\_Max\_ge\_6)] + (N) + \varepsilon}$ Second Model Equation for middle BP tertile in F/W/S season: $\hat{\beta}_0 = -6.2028$; $\hat{\beta}_1 = 1.0064$ and $\hat{\beta}_2 = 0.5680$.

| Model Information | |
|---|---|
| Data Set | WORK.FWS_AVG_BP_2 |
| Distribution | Poisson |
| Link Function | Log |
| Dependent Variable | Upper_Tertile_FWS |
| Offset Variable | LN_N |

| GEE Model Information | |
|---|---|
| Correlation Structure | Independent |
| Within-Subject Effect | ID (205 levels) |
| Subject Effect | Date (91 levels) |
| Number of Clusters | 91 |
| Correlation Matrix Dimension | 205 |
| Maximum Cluster Size | 92 |
| Minimum Cluster Size | 35 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −6.2028 | 0.4588 | −7.1021 | −5.3035 | −13.52 | <.0001 |
| BP_Diff_Mean_Low | 1 | 1.0064 | 0.3913 | 0.2395 | 1.7733 | 2.57 | 0.0101 |
| WS_Diff_Max_ge_6 | 1 | 0.5680 | 0.4610 | −0.3355 | 1.4716 | 1.23 | 0.2179 |

| Model | Parameter | Variable | RR | Lower 95% Cl | Upper 95% Cl | p-value |
|---|---|---|---|---|---|---|
| Cut-points | BP 24 Hr diff Mean ≤ −0.05 | Yes vs. No | 2.74 | 1.27 | 5.89 | 0.01 |
| | WS 24 hr_diff Max ≥ 6 | Yes vs. No | 1.76 | 0.72 | 4.36 | 0.22 |

$\log(UT\text{-}IR\text{-}NOH \text{ Day}) = \beta_0 + \beta_1(BP\_Diff\_Mean\_Low) + \beta_2(WS\_Diff\_Max\_ge\_6) + \log(N)$ Second Model Equation:

Or equivalently, $UT\text{-}IR\text{-}NOH \text{ Day} = e^{[\beta_0 + \beta_1(BP\_Diff\_Mean\_Low) + \beta_2(WS\_Diff\_Max\_ge\_6)] + (N) + \varepsilon}$ Similarly, a Third and Fourth Model Equation were generated and are set forth below:
24 HR BP diff mean<=−0.05 and RH mean>=79

$\log(\text{Upper Tertile Headache Day}) = \beta_0 + \beta_1(BP\_Diff\_Mean\_Low) + \beta_2(RH\_Daily\_Mean\_ge\_79) + \log(N) + \varepsilon$ Third Model Equation:

Or equivalently,

Upper Tertile Headache Day=
$\beta^{[\beta_0 + \beta_1(BP\_Diff\_Mean\_Low) + \beta_2(RH\_Daily\_Mean\_ge\_79)]} + \log(N) + \varepsilon$ $\log(\text{Upper Tertile Headache Day}) = \beta_0 + \beta_1(BP\_24h\_Diff\_Mean\_le\_0.10) + \beta_2(RH\_Daily\_Mean\_ge\_78) + \log(N) + \varepsilon$ Fourth Model Equation:

Or equivalently,

Upper Tertile Headache Day=$e^{[\beta_0 + \beta_1(BP\_24h\_Diff\_Mean\_le\_\leq 0.10) + \beta_2(RH\_Daily\_Mean\_ge\_78)] + (N) + \varepsilon}$ In other specific embodiments the significant weather variables are BP_24h_Diff_Mean_le_neg_0.05 and RH_Daily_Mean_ge_79

Example 4

This example illustrates generation of model equations for upper tertile BP days in the F/W/S season,
For the first and second model equations:

Outcome variable: UT-IR-NOH
  1=Yes; the day is a UT-IR-NOH day for the season
  0=No; the day is not a UT-IR-NOH day for the season
  The intercept is represented by $\beta_0$
First predictor variable: BP_Diff_Mean_High
  1=Yes; the day had a BP_24hr_Diff_Mean≥0.10
  0=No; the day did not have a BP_24hr_Diff_Mean≥0.10
  The coefficient for the predictor variable BP_Diff_Mean_High is represented by $\beta_1$
Second predictor variable: DBT_24hr_diff_mean_cutpoint
  1=Yes; the day had a DBT_24hr_diff_mean≤−5
  0=No; the day did NOT have a DBT_24hr_diff_mean≤−5
  The coefficient for the predictor variable DBT_24hr_diff_mean_cutpoint is represented by $\beta_2$
Offset term—variable log(N), where N=the number of patients eligible to have a NOH on the given day.
Error term of GEE regression model represented by "$\varepsilon$".
First Model Equation for upper BP tertile in the F/W/S season: $\hat{\beta}_0 = -6.7779$; $\hat{\beta}_1 = 1.5806$ and $\hat{\beta}_2 = 1.2285$.

| Model Information | |
| --- | --- |
| Data Set | WORK.FWS_HIGH_BP_1 |
| Distribution | Poisson |
| Link Function | Log |
| Dependent Variable | Upper_Tertile_FWS |
| Offset Variable | LN_N |
| GEE Model Information | |
| Correlation Structure | Independent |
| Within-Subject Effect | ID (206 levels) |
| Subject Effect | Date (92 levels) |
| Number of Clusters | 92 |
| Correlation Matrix Dimension | 206 |
| Maximum Cluster Size | 98 |
| Minimum Cluster Size | 35 |

Analysis Of GEE Parameter Estimates
Empirical Standard Error Estimates

| Parameter | | Estimate | Standard Error | 95% Confidence Limits | | Z | Pr > |Z| |
| --- | --- | --- | --- | --- | --- | --- | --- |
| Intercept | | −6.7779 | 0.4418 | −7.6439 | −5.9120 | −15.34 | <.0001 |
| BP_Diff_Mean_cutpoint | 1 | 1.5806 | 0.4979 | 0.6047 | 2.5565 | 3.17 | 0.0015 |
| DBT_24Hr_Mean_cutpoint | 1 | 1.2285 | 0.3617 | 0.5196 | 1.9374 | 3.40 | 0.0007 |

| Model | Parameter | Variable | RR | Lower 95% Cl | Upper 95% Cl | p-value |
| --- | --- | --- | --- | --- | --- | --- |
| Cut-points | BP_24 Hr diff Mean ≥ 0.10 | Yes vs. No | 4.86 | 1.83 | 12.89 | <0.01 |
| | DBT_24 Hr diff Mean ≤ −5 | Yes vs. No | 3.42 | 1.68 | 6.94 | <0.01 |

$$\log(UT\text{-}IR\text{-}NOH\ Day) = \beta_0 + \beta_1(BP\_Diff\_Mean\_High) + \beta_2(DBT\_24hr\_diff\_Mean\_cutpoint) + \log(N) + \varepsilon$$

First Model Equation:

Or equivalently, $$UT\text{-}IR\text{-}NOH\ Day = e^{[\beta_0 + \beta_1(BP\_Diff\_Mean\_High) + \beta_2(DBT\_24hr\_diff\_Mean\_cutpoint)]} + (N) + \varepsilon$$

Second Model Equation for upper BP tertile, F/W/S season, $\hat{\beta}_0 = -6.7684$; $\hat{\beta}_1 = 1.8818$ and $\hat{\beta}_2 = 0.6563$.
For this equation, the second predictor variable changes.

Second predictor variable: DBT_6hr_diff_mean_cutpoint
  1=Yes; the day had a DBT_6hr_diff_mean≤−5
  0=No; the day did NOT have a DBT_6hr_diff_mean≤−5
The coefficient for the predictor variable DBT_6hr_diff_mean_cutpoint is represented by $\beta_2$

| Model Information | |
| --- | --- |
| Data Set | WORK.FWS_UPPER_BP_2 |
| Distribution | Poisson |
| Link Function | Log |
| Dependent Variable | Upper_Tertile_FWS |
| Offset Variable | LN_N |
| GEE Model Information | |
| Correlation Structure | Independent |
| Within-Subject Effect | ID (206 levels) |
| Subject Effect | Date (92 levels) |
| Number of Clusters | 92 |
| Correlation Matrix Dimension | 206 |

-continued

| | |
|---|---|
| Maximum Cluster Size | 98 |
| Minimum Cluster Size | 35 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −6.7684 | 0.4813 | −7.7118 | −5.8250 | −14.06 | <.0001 |
| BP_Diff_Mean_cutpoint | 1 | 1.8818 | 0.4903 | 0.9208 | 2.8427 | 3.84 | 0.0001 |
| DBT_6Hr_Mean_cutpoint | 1 | 0.6563 | 0.3428 | −0.0155 | 1.3281 | 1.91 | 0.0555 |

| Model | Parameter | Variable | RR | Lower 95% Cl | Upper 95% Cl | p-value |
|---|---|---|---|---|---|---|
| Cut-points | BP_24 hr diff Mean ≥ 0.10 | Yes vs. No | 6.57 | 2.51 | 17.16 | <0.01 |
| | DBT 6 HR diff Mean ≤ −0.5 | Yes vs. No | 1.93 | 0.98 | 3.77 | 0.06 |

$$\log(UT\text{-}IR\text{-}NOH\ Day) = \beta_0 + \beta_1(BP\_Diff\_Mean\_High) + \beta_2(DBT\_6hr\_diff\_Mean\_cutpoint) + \log(N) + \varepsilon$$

Second Model Equation:

Or equivalently, $$UT\text{-}IR\text{-}NOH\ Day = e^{[\beta_0 + \beta_1(BP\_Diff\_Mean\_High) + \beta_2(DBT\_6hr\_diff\_Mean\_cutpoint)]} + (N) + \varepsilon$$

Similarly, a third model equation for UT-BP F/SW was generated:

$$\log(\text{Upper Tertile Headache Day}) = \beta_0 + \beta_1(BP\_Diff\_Mean\_High) + \beta_2(RH\_Diff\_Min\_le\_neg\_25) + \log(N) + \varepsilon$$

Or equivalently, $$\text{Upper Tertile Headache Day} = e^{[\beta_0 + \beta_1(BP\_Diff\_Mean\_High) + \beta_2(RH\_Diff\_Min\_le\_neg\_25)]} + (N) + \varepsilon$$

In other specific embodiments the significant weather variables were BP_Diff_Mean_ge_0.10 and RH_Diff_Min_le_neg_25

Example 5

This example illustrates generation of model equations for lower tertile BP days in the Summer season.

Outcome variable: UT-IR-NOH
 1=Yes; the day is a UT-IR-NOH day for the season
 0=No; the day is not a UT-IR-NOH day for the season
 The intercept is represented by $\beta_0$
First predictor variable: BP_Diff_Max_Low
 1=Yes; the day had a BP_24hr_Diff_Max≤−0.01
 0=No; the day did not have a BP_24hr_Diff_Max≤−0.01
 The coefficient for the predictor variable BP_Diff_Max_Low is represented by $\beta_1$
Offset term—variable log(N), where N=the number of patients eligible to have a NOH on the given day.
Error term of GEE regression model represented by "ε".
First Model Equation for lower BP tertile in the Summer season: $\hat{\beta}_0 = -4.9774$, $\hat{\beta}_1 = 1.3396$

| Model Information | |
|---|---|
| Data Set | WORK.SUMMER_LOW_1 |
| Distribution | Poisson |
| Link Function | Log |
| Dependent Variable | Upper_Tertile_Summer_both |
| Offset Variable | LN_N |
| GEE Model Information | |
| Correlation Structure | Independent |
| Within-Subject Effect | ID (111 levels) |
| Subject Effect | Date (47 levels) |
| Number of Clusters | 47 |
| Correlation Matrix Dimension | 111 |
| Maximum Cluster Size | 55 |
| Minimum Cluster Size | 15 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −4.9774 | 0.4198 | −5.8001 | −4.1547 | −11.86 | <.0001 |
| BP_24hr_Max_cutpoint | 1 | 1.3396 | 0.4594 | 0.4392 | 2.2400 | 2.92 | 0.0035 |

| Model | Parameter | Variable | RR | Lower 95% CI | Upper 95% CI | p-value |
|---|---|---|---|---|---|---|
| Cut-point | BP 24 hr Max ≤ −0.01 | Yes vs. No | 3.82 | 1.55 | 9.39 | <0.01 |

$$\log(UT\text{-}IR\text{-}NOH \text{ Day}) = \beta_0 + \beta_1(BP\_Diff\_Max\_Low) + \log(N) + \varepsilon$$

First Model Equation:

Or equivalently, $$UT\text{-}IR\text{-}NOH \text{ Day} = e^{[\beta_0 + \beta_1(BP\_Diff\_Max\_Low)]} + (N) + \varepsilon$$

Second Model Equation for lower BP tertile, Summer season: $\hat{\beta}_0 = -5.3481$, $\hat{\beta}_1 = 1.7615$

| Model Information | |
|---|---|
| Data Set | WORK.SUMMER_LOW_2 |
| Distribution | Poisson |
| Link Function | Log |
| Dependent Variable | Upper_Tertile_Summer_both |
| Offset Variable | LN_N |
| GEE Model Information | |
| Correlation Structure | Independent |
| Within-Subject Effect | ID (111 levels) |
| Subject Effect | Date (47 levels) |
| Number of Clusters | 47 |
| Correlation Matrix Dimension | 111 |
| Maximum Cluster Size | 55 |
| Minimum Cluster Size | 15 |

Analysis Of GEE Parameter Estimates
Empirical Standard Error Estimates

| Parameter | | Estimate | Standard Error | 95% Confidence Limits | | Z | Pr > |Z| |
|---|---|---|---|---|---|---|---|
| Intercept | | −5.3481 | 0.5194 | −6.3661 | −4.3302 | −10.30 | <.0001 |
| BP_24hr_Max_cutpoint | 1 | 1.7615 | 0.5473 | 0.6887 | 2.8343 | 3.22 | 0.0013 |

| Model | Parameter | Variable | RR | Lower 95% CI | Upper 95% CI | p-value |
|---|---|---|---|---|---|---|
| Cut-point | BP 24 hr Max ≤ 0.00 | Yes vs. No | 5.82 | 1.99 | 17.02 | <0.01 |

$$\log(UT\text{-}IR\text{-}NOH \text{ Day}) = \beta_0 + \beta_1(BP\_Diff\_Max\_Low) + \log(N) + \varepsilon$$

Second Model Equation:

Or equivalently, $$(UT\text{-}IR\text{-}NOH \text{ Day}) = e^{[\beta_0 + \beta_1(BP\_Diff\_Max\_Low)]} + (N) + \varepsilon$$

Example 6

This example illustrates generation of model equations for middle tertile BP days in the Summer season.
Outcome variable: UT-IR-NOH
  1=Yes; the day is a UT-IR-NOH day for the season
  0=No; the day is not a UT-IR-NOH day for the season
  The intercept is represented by $\beta_0$
First predictor variable: BP_Daily_Mean_Low
  1=Yes; the day had a BP_Daily_Mean≤29.44
  0=No; the day did not have a BP_Daily_Mean≤29.44
The coefficient for the predictor variable BP_Daily_Mean_Low is represented by $\beta_1$
Second predictor variable: DBT_Daily_Mean_le_77
  1=Yes; the day had a DBT_Daily_Mean≤77
  0=No; the day did not have a DBT_Daily_Mean≤77
The coefficient for the predictor variable DBT_Daily_Mean_le_77 is represented by $\beta_2$
Offset term—variable log(N), where N=the number of patients eligible to have a NOH on the given day.
Error term of GEE regression model represented by "$\varepsilon$".
First Model Equation for middle BP tertile in the Summer season: $\hat{\beta}_0 = -5.5947$, $\hat{\beta}_1 = 1.2594$, $\hat{\beta}_2 = 1.2393$

| Model Information | |
|---|---|
| Data Set | WORK.SUMMER_MIDDLE_1 |
| Distribution | Poisson |
| Link Function | Log |
| Dependent Variable | Upper_Tertile_Summer_both |
| Offset Variable | LN_N |
| GEE Model Information | |
| Correlation Structure | Independent |
| Within-Subject Effect | ID (108 levels) |
| Subject Effect | Date (48 levels) |
| Number of Clusters | 48 |

| | |
|---|---|
| Correlation Matrix Dimension | 108 |
| Maximum Cluster Size | 54 |
| Minimum Cluster Size | 15 |

Analysis Of GEE Parameter Estimates
Empirical Standard Error Estimates

| Parameter | | Estimate | Standard Error | 95% Confidence Limits | | Z | Pr > |Z| |
|---|---|---|---|---|---|---|---|
| Intercept | | −5.5947 | 0.4338 | −6.4449 | −4.7445 | −12.90 | <.0001 |
| BP_Daily_Mean_cutpoi | 1 | 1.2594 | 0.4261 | 0.4242 | 2.0945 | 2.96 | 0.0031 |
| DBT_Daily_Mean_cutpo | 1 | 1.2393 | 0.3827 | 0.4892 | 1.9893 | 3.24 | 0.0012 |

| Model | Parameter | Variable | RR | Lower 95% CI | Upper 95% CI | p-value |
|---|---|---|---|---|---|---|
| Cut-point | BP Daily Mean ≤ 29.44 | Yes vs. No | 3.52 | 1.53 | 8.12 | <0.01 |
| | DBT Daily Mean ≤ 77 | Yes vs. No | 3.45 | 1.63 | 7.31 | <0.01 |

$$\log(UT\text{-}IR\text{-}NOH\ \text{Day}) = \beta_0 + \beta_1(BP\_Daily\_Mean\_Low) + \beta_2(DBT\_Daily\_Mean\_le\_77) + \log(N) + \varepsilon$$ First Model Equation:

Or equivalently, $$UT\text{-}IR\text{-}NOH\ \text{Day} = e^{[\beta_0 + \beta_1(BP\_Daily\_Mean\_Low) + \beta_2(DBT\_Daily\_Mean\_le\_77)]} + (N) + \varepsilon$$

Example 7

This example illustrates generation of model equations for upper tertile BP days in the Summer season.
Outcome variable: UT-IR-NOH
  1=Yes; the day is a UT-IR-NOH day for the season
  0=No; the day is not a UT-IR-NOH day for the season
  The intercept is represented by $\beta_0$
First predictor variable: RH_Diff_Mean_ge_5
  1=Yes; the day had a RH_24hr_Diff_Mean≥5
  0=No; the day did not have a RH_24hr_Diff_Mean≥5
  The coefficient for the predictor variable RH_Diff_Mean_ge_5 is represented by $\beta_1$
Offset term—variable log(N), where N=the number of patients eligible to have a NOH on the given day.
Error term of GEE regression model represented by "$\varepsilon$".
First Model Equation for upper BP tertile in the Summer season: $\hat{\beta}_0 = -4.5228$, $\hat{\beta}_1 = 1.1376$

| Model Information | |
|---|---|
| Data Set | WORK.SUMMER_UPPER_1 |
| Distribution | Poisson |
| Link Function | Log |
| Dependent Variable | Upper_Tertile_Summer_both |
| Offset Variable | LN_N |

| GEE Model Information | |
|---|---|
| Correlation Structure | Independent |
| Within-Subject Effect | ID (108 levels) |
| Subject Effect | Date (48 levels) |
| Number of Clusters | 48 |
| Correlation Matrix Dimension | 108 |
| Maximum Cluster Size | 54 |
| Minimum Cluster Size | 14 |

Analysis Of GEE Parameter Estimates
Empirical Standard Error Estimates

| Parameter | | Estimate | Standard Error | 95% Confidence Limits | | Z | Pr > |Z| |
|---|---|---|---|---|---|---|---|
| Intercept | | −4.5228 | 0.2916 | −5.0944 | −3.9512 | −15.51 | <.0001 |
| RH_24Hr_Mean_cutpoin | 1 | 1.1376 | 0.3266 | 0.4974 | 1.7778 | 3.48 | 0.0005 |

| Model | Parameter | Variable | RR | Lower 95% Cl | Upper 95% Cl | p-value |
|---|---|---|---|---|---|---|
| Cut-point | RH 24 hr Mean ≥ 5 | Yes vs. No | 3.12 | 1.64 | 5.92 | <0.01 |

$$\log(UT\text{-}IR\text{-}NOH \text{ Day}) = \beta_0 + \beta_1(RH\_Diff\_Mean\_ge\_5) + \log(N) + \varepsilon \quad \text{First Model Equation:}$$

Or equivalently, $$UT\text{-}IR\text{-}NOH \text{ Day} = e^{[\beta_0 + \beta_1(RH\_Diff\_Mean\_ge\_5)]} + (N) + \varepsilon$$

Second Model Equation for upper BP tertile in the Summer season: $\hat{\beta}_0 = -4.5292$, $\hat{\beta}_1 = 1.1860$

| Model Information | |
|---|---|
| Data Set | WORK.SUMMER_HIGH_2 |
| Distribution | Poisson |
| Link Function | Log |
| Dependent Variable | Upper_Tertile_Summer_both |
| Offset Variable | LN_N |
| GEE Model Information | |
| Correlation Structure | Independent |
| Within-Subject Effect | ID (108 levels) |
| Subject Effect | Date (48 levels) |
| Number of Clusters | 48 |
| Correlation Matrix Dimension | 108 |
| Maximum Cluster Size | 54 |
| Minimum Cluster Size | 14 |

Analysis Of GEE Parameter Estimates
Empirical Standard Error Estimates

| Parameter | | Estimate | Standard Error | 95% Confidence Limits | | Z | Pr > \|Z\| |
|---|---|---|---|---|---|---|---|
| Intercept | | −4.5292 | 0.2917 | −5.1009 | −3.9575 | −15.53 | <.0001 |
| RH_24Hr_Mean_cutpoin | 1 | 1.1860 | 0.3250 | 0.5491 | 1.8229 | 3.65 | 0.0003 |

| Model | Parameter | Variable | RR | Lower 95% Cl | Upper 95% Cl | p-value |
|---|---|---|---|---|---|---|
| Cut-point | RH 24 hr Mean ≥ 7 | Yes vs. No | 3.27 | 1.73 | 6.19 | <0.01 |

$$\log(UT\text{-}IR\text{-}NOH \text{ Day}) = \beta_0 + \beta_1(RH\_Diff\_Mean\_ge\_7) + \log(N) + \varepsilon \quad \text{Second Model Equation:}$$

Or equivalently, $$UT\text{-}IR\text{-}NOH \text{ Day} = e^{[\beta_0 + \beta_1(RH\_Diff\_Mean\_ge\_7)]} + (N) + \varepsilon$$

Example 8

The following Example utilizes a bootstrap analysis to provide initial validation of the models developed for low, average and high BP days for the Fall/Winter/Spring season.

In a bootstrap analysis, the original data is re-sampled to create a new data set. The new data set has some observations from the original data repeated multiple times, while some observations in the original data set may not be selected in the new data set. The process is repeated hundreds or thousands of times to get a large number of "bootstrap" data sets which are all based on the original data set. A regression analysis is run for each bootstrap data set and results are obtained. The results are used to estimate each of the statistics involved in the regression analysis. For example, if regression analysis is conducted on 1,000 bootstrap samples generated from the Low BP data set, 1,000 different estimates of the RR value for the BP 24-hour difference variable may be obtained (i.e., one RR estimate from each bootstrap data set). The 2.5$^{th}$ and 97.5$^{th}$ percentiles of these 1,000 RR estimates are used to obtain a bootstrap 95% confidence interval for the RR estimate of the BP 24-hour difference variable.

The original data set included multiple observations for each subject; hence rather than re-sampling from each observation, various subjects within each BP tertile were re-sampled. Each time a subject is selected in the bootstrap process, all of the measurements belonging to that subject are selected. In this way, the within-subject and between-subject covariance structure of the original data set is maintained. Because some subjects had missing observations for one or more variables, the bootstrap (or replicate) data sets also contained some missing observations. Since some subjects had more observation days than others, each of the bootstrap data sets will not have the exact same number of observations.

It was previously observed that the best variables for the Lower, Middle, and Upper BP tertile days were as follows:

Lower BP→1) BP 24-hour difference Mean+2) Wind Speed 24-hour difference Maximum

Middle BP→1) BP 24-hour difference Mean+2) Wind Speed 24-hour difference Maximum Upper BP→1) BP 24-hour difference Mean+2) Dry Bulb Temp. 24-hour difference Mean For each BP tertile, a generalized additive model (GAM) using the original data set was performed to determine the potential cut-points for each variable. A GEE regression analysis was performed for the "best" cut-point model using the original data set. The results of the GAM and GEE analyses for Lower. Middle and Upper Barometric Pressure (BP) days are set forth in FIG. 5A-B, FIG. 6A-B and FIG. 7A-B, respectively.

Based on the potential cut-points from the GAM analyses, several GEE analyses using the bootstrap data sets were performed using different combinations of cut-points for the two variables. For each BP tertile, 1,000 bootstrap data sets were generated. The GEE regression analysis was performed for each bootstrap data set. Based on the results of the 1,000 data sets, the bootstrap 95% confidence intervals were determined for each statistic in the GEE regression.

The following cut-point combinations were assessed in the bootstrap analysis:

| Lower BP | Middle BP | Upper BP |
|---|---|---|
| BP ≤ 0.0, WS ≥ 7 | BP ≤ 0.0, WS ≥ 6 | BP > 0.1, DBT < −10 |
| BP ≤ 0.0, WS ≥ 11 | BP ≤ 0.0, WS ≥ 8 | BP > 0.1, DBT < −5 |
| BP ≤ 0.0, WS ≥ 15 | BP ≤ 0.0, WS ≥ 11 | BP > 0.1, DBT < 0 |
| BP ≤ 0.1, WS ≥ 7 | BP ≤ 0.1, WS ≥ 6 | BP > 0.1, DBT < 5 |
| BP ≤ 0.1, WS ≥ 11 | BP ≤ 0.1, WS ≥ 8 | BP > 0.3, DBT < −10 |
| BP ≤ 0.1, WS ≥ 15 | BP ≤ 0.1, WS ≥ 11 | BP > 0.3, DBT < −5 |
| BP ≤ −0.1, WS ≥ 7 | BP ≤ −0.1, WS ≥ 6 | BP > 0.3, DBT < 0 |
| BP ≤ −0.1, WS ≥ 11 | BP ≤ −0.1, WS ≥ 8 | BP > 0.3, DBT < 5 |
| BP ≤ −0.1, WS ≥ 15 | BP ≤ −0.1, WS ≥ 11 | BP > 0.4, DBT < −10 |
| BP ≤ −0.2, WS ≥ 7 | BP ≤ −0.2, WS ≥ 6 | BP > 0.4, DBT < −5 |
| BP ≤ −0.2, WS ≥ 11 | BP ≤ −0.2, WS ≥ 8 | BP > 0.4, DBT < 0 |
| BP ≤ −0.2, WS ≥ 15 | BP ≤ −0.2, WS ≥ 11 | BP > 0.4, DBT < 5 |
| BP ≤ −0.3, WS ≥ 7 | | |
| BP ≤ −0.3, WS ≥ 11 | | |
| BP ≤ −0.3, WS ≥ 15 | | |

Results of each combination of cut-points were compared and the "best" bootstrap models were selected. The output for the models selected are summarized in FIG. 5C for Lower BP tertile days, FIG. 6C for Middle BP tertile days, and FIG. 7C for Upper BP tertile days. For each predictor variable, the output consists of the mean value and 95% confidence interval for the following statistics: the RR estimate, the Lower Cl of the RR, the Upper Cl of the RR, the p-value estimate, and the QIC fit statistic estimate.

For example, in the analysis of the Lower BP tertile days (FIGS. 5A and B) there appeared to be two models that performed better than the rest. The first of these models involved using the cut-points of BP 24-hour difference mean≤0.0 and WS 24-hour difference Max≥7. The bootstrap analysis results for this model are summarized in Model 1 of FIG. 5C. The mean RR estimate for the BP variable across the 1,000 bootstrap data sets are 3.24. The 95% confidence interval for this RR estimate across the 1,000 bootstrap data sets was (2.83, 3.78). The mean estimate of the Lower Cl for the RR of the BP variable was 1.32 with a 95% Cl of (1.20, 1.47), across the 1,000 bootstrap data sets. The other results for the other statistics can be interpreted in a similar fashion.

Example 9

Figure 1:
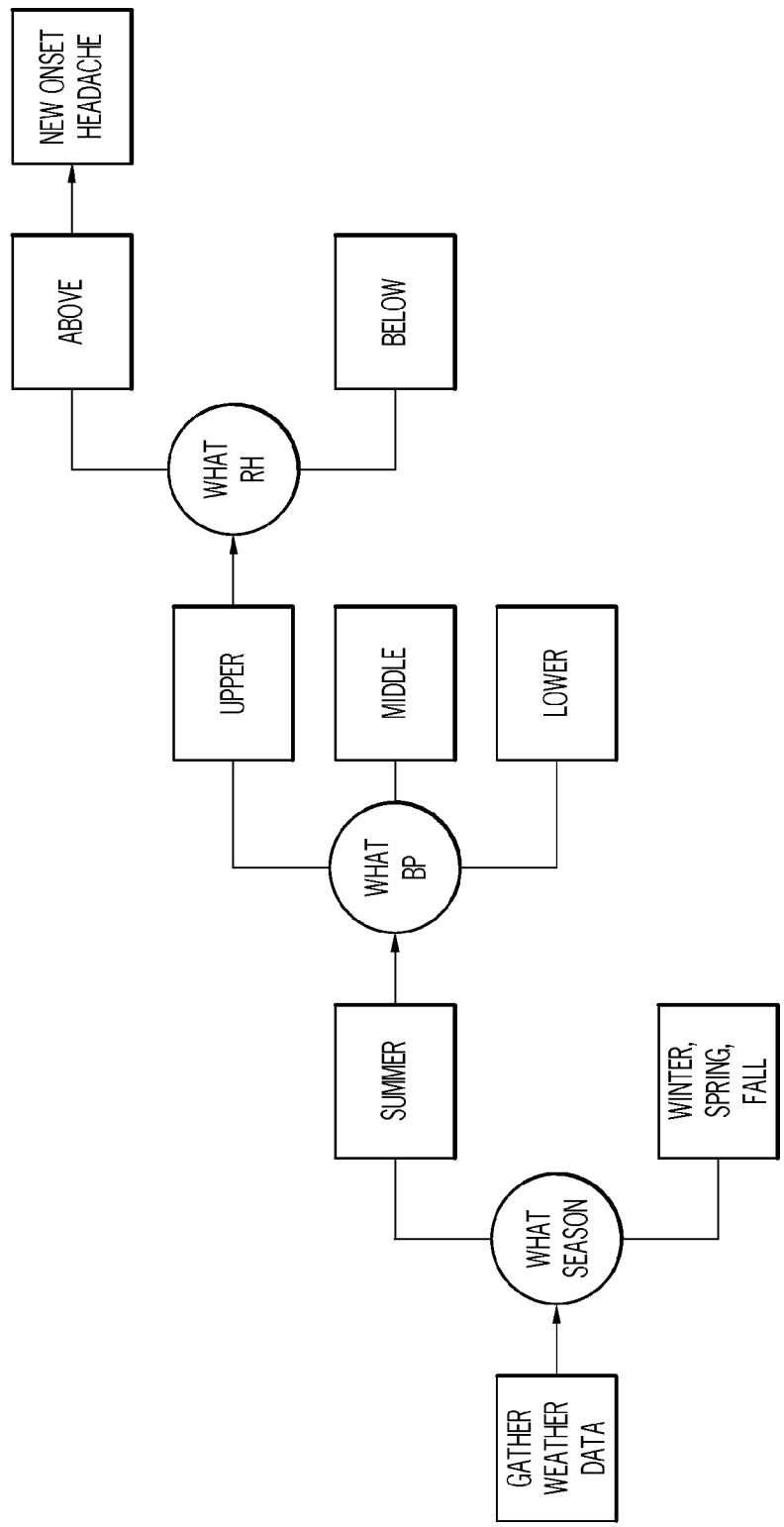
FIG. 1. Depicts a schematic flow chart of general data input steps in the model for predicting risk of a new onset headache.
Figure 2:
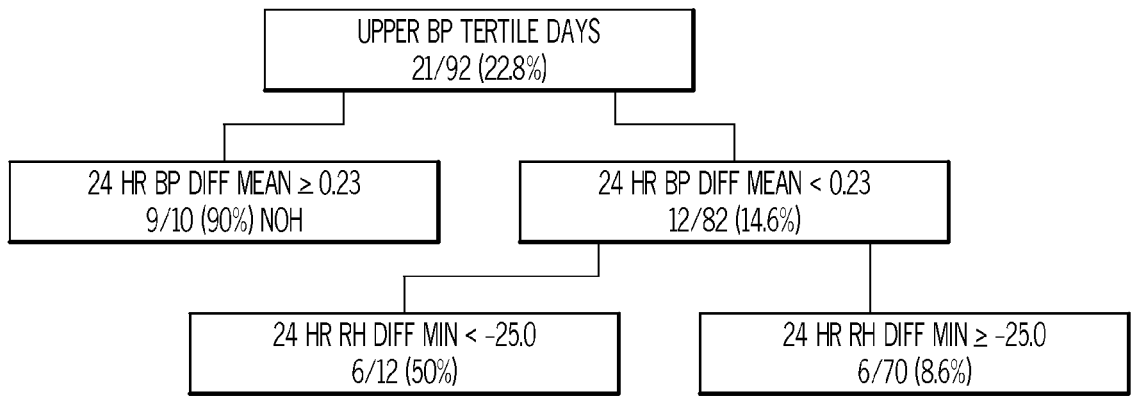
FIG. 2. An empirically generated flow-chart showing percentage of upper BP tertile days during the F/W/S season in which a New Onset Headache (NOH) was experienced as a function of particular weather variables.
Figure 3:
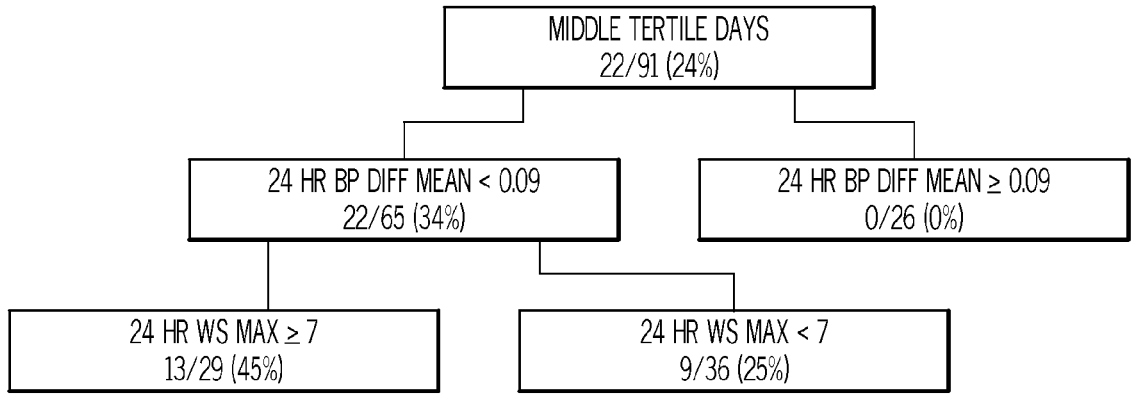
FIG. 3. An empirically generated flow-chart showing percentage of middle BP tertile days during the F/W/S season in which an NOH occurred as a function of particular weather variables.
Figure 4:
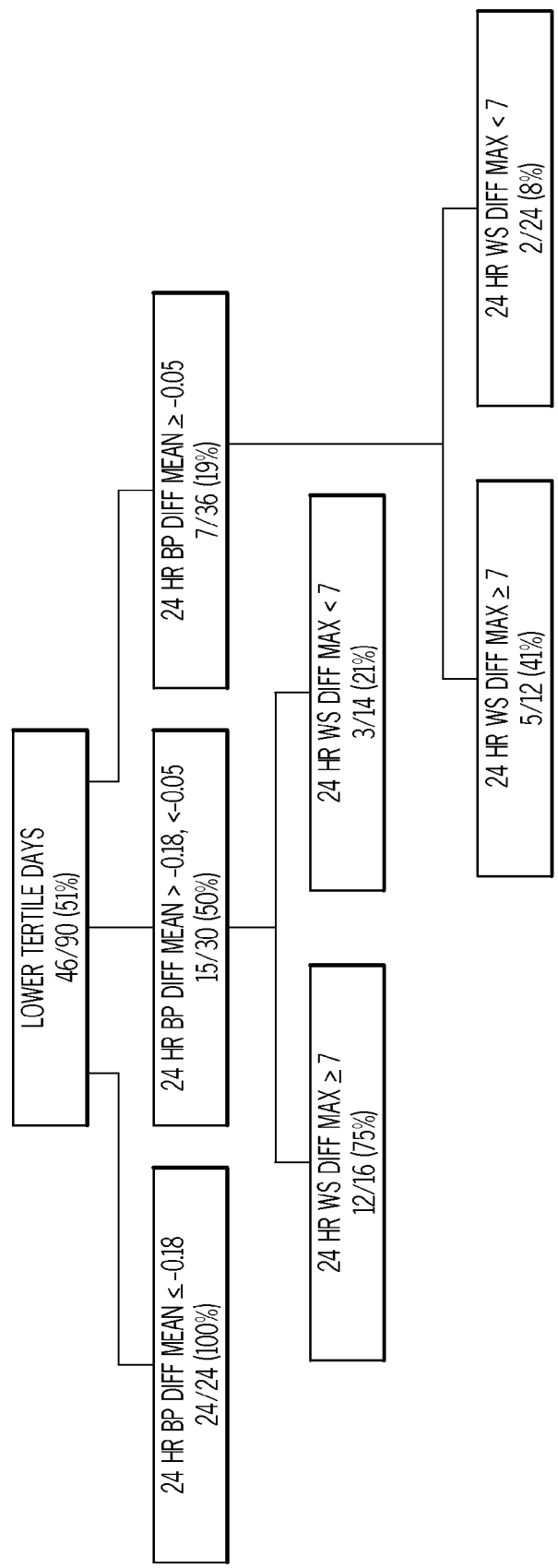
FIG. 4. An empirically generated flow-chart showing percentage of lower BP tertile days during the F/W/S season in which an NOH occurred as a function of particular weather variables.
Figure 5A:
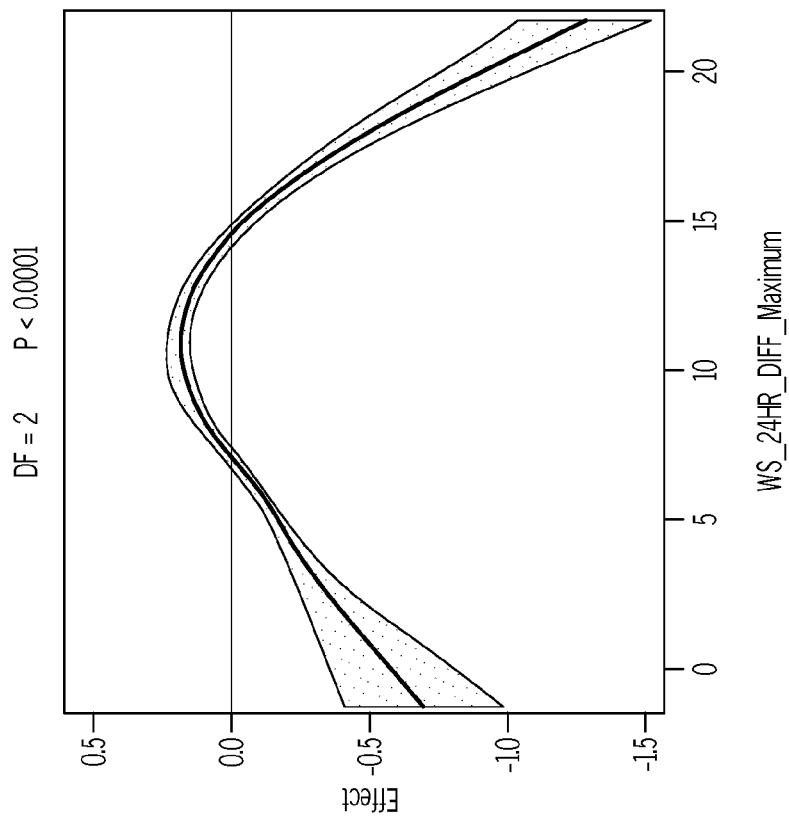
FIG. 5. 5A) Generalized Additive Model (GAM) based on the original data set for lower BP tertile in the F/W/S season; 5B) Generalized Estimating Equation model based on the same original data set; 5C) two best Bootstrap Models for re-sampled data.
Figure 5A:
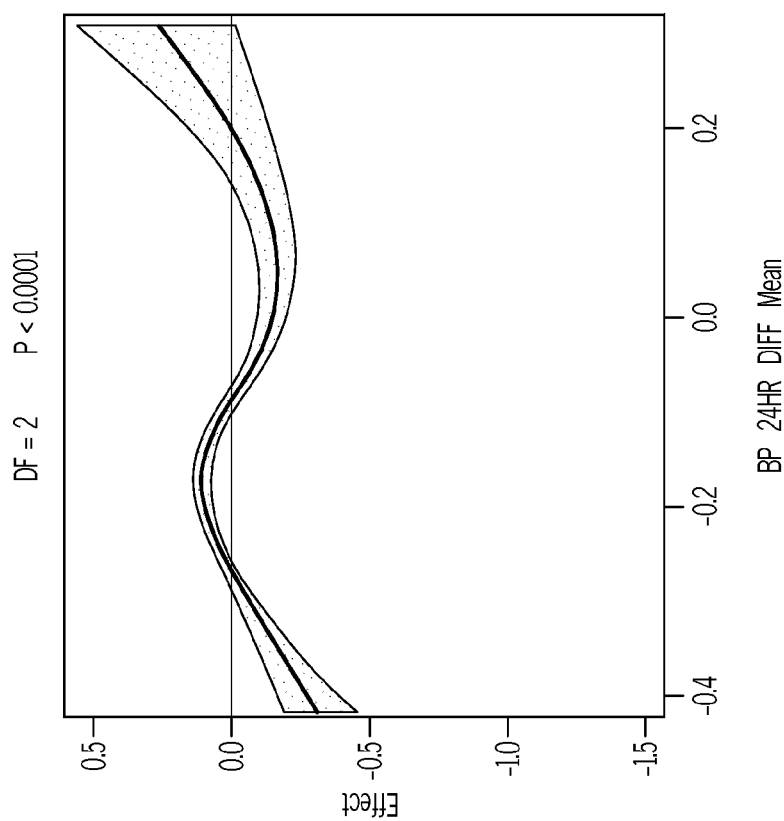
Figure 6A:
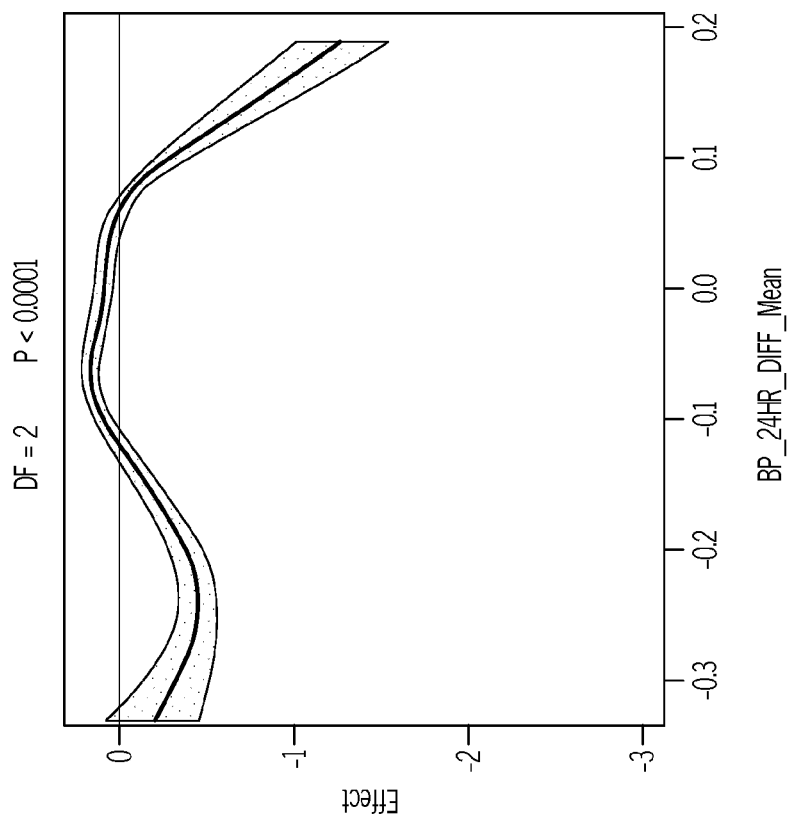
FIG. 6. 6A) Generalized Additive Model (GAM) based on the original data set for middle BP tertile in the F/W/S season; 6B) Generalized Estimating Equation model based on the same original data set; 6C) best Bootstrap Model for re-sampled data.
Figure 6A:
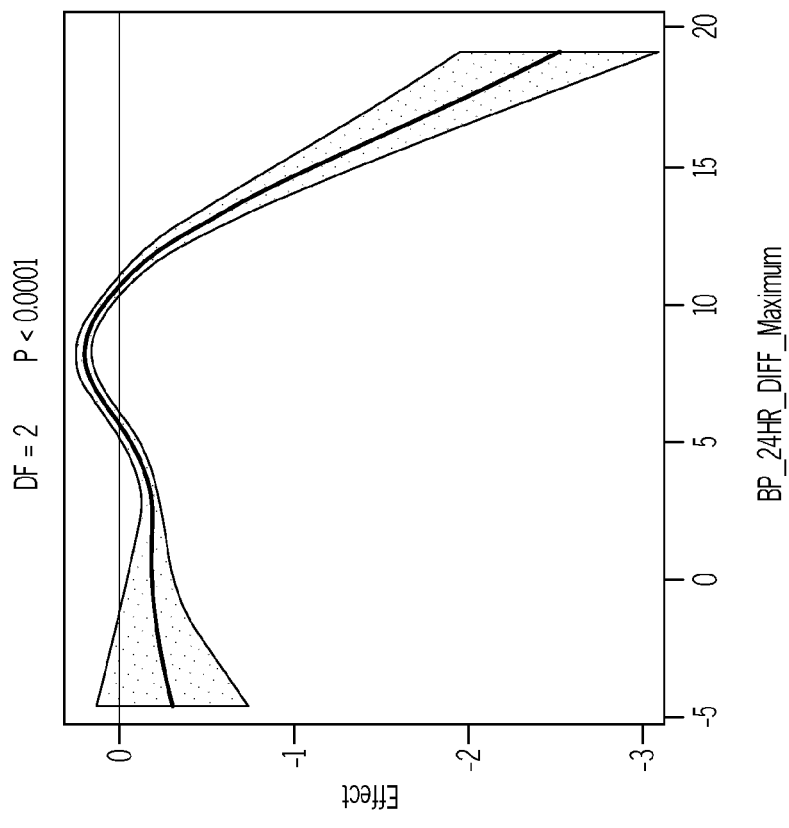
Figure 7A:
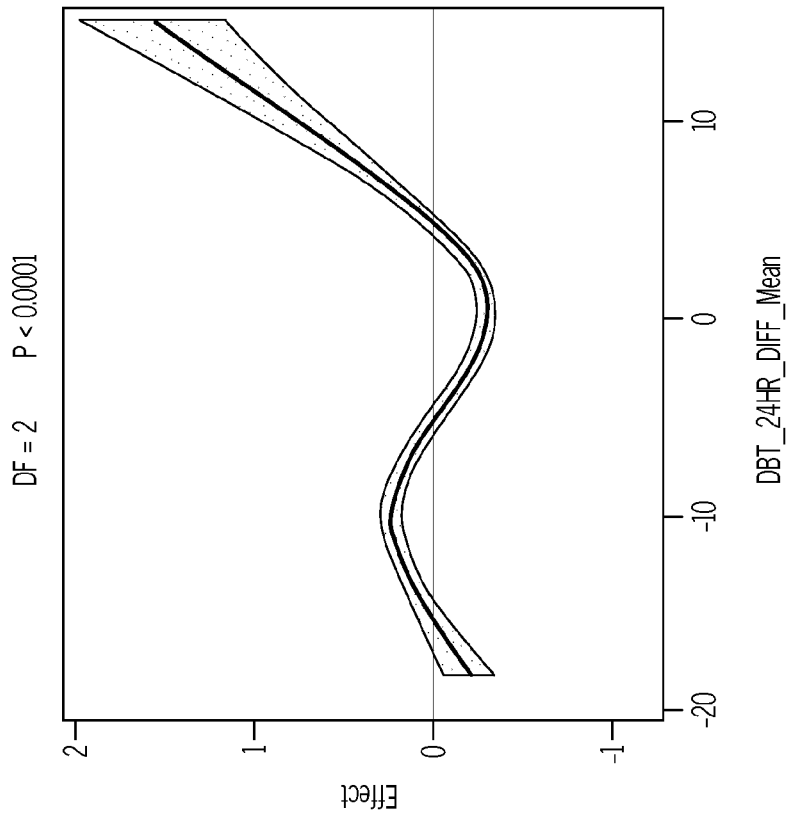
FIG. 7. 7A) Generalized Additive Model (GAM) based on the original data set for upper BP tertile in the F/W/S season; 7B) Generalized Estimating Equation model based on the same original data set; 7C) three best Bootstrap Models for re-sampled data.
Figure 7A:
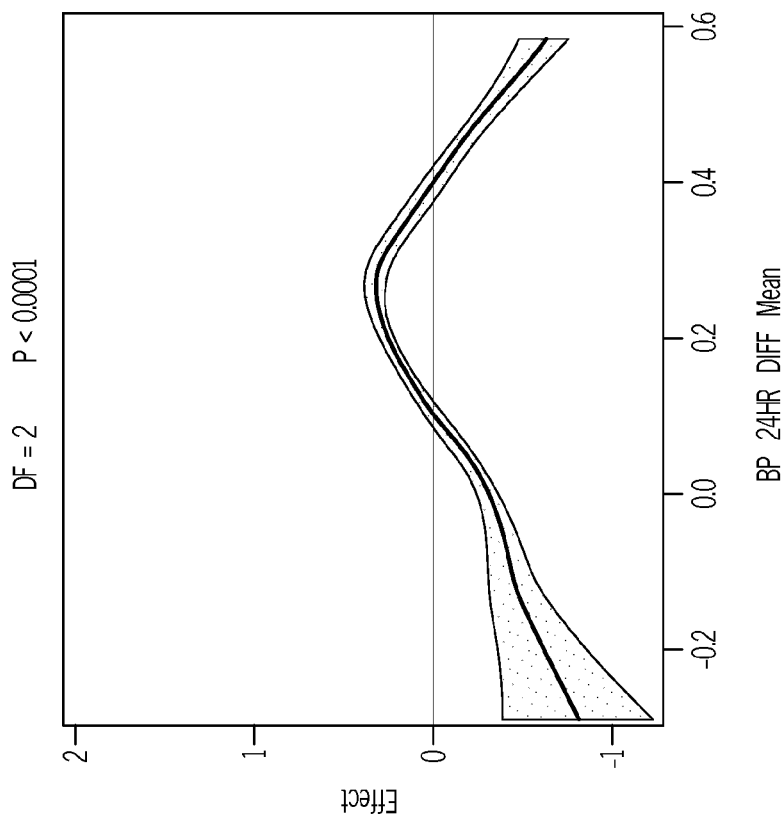
Figure 8A:
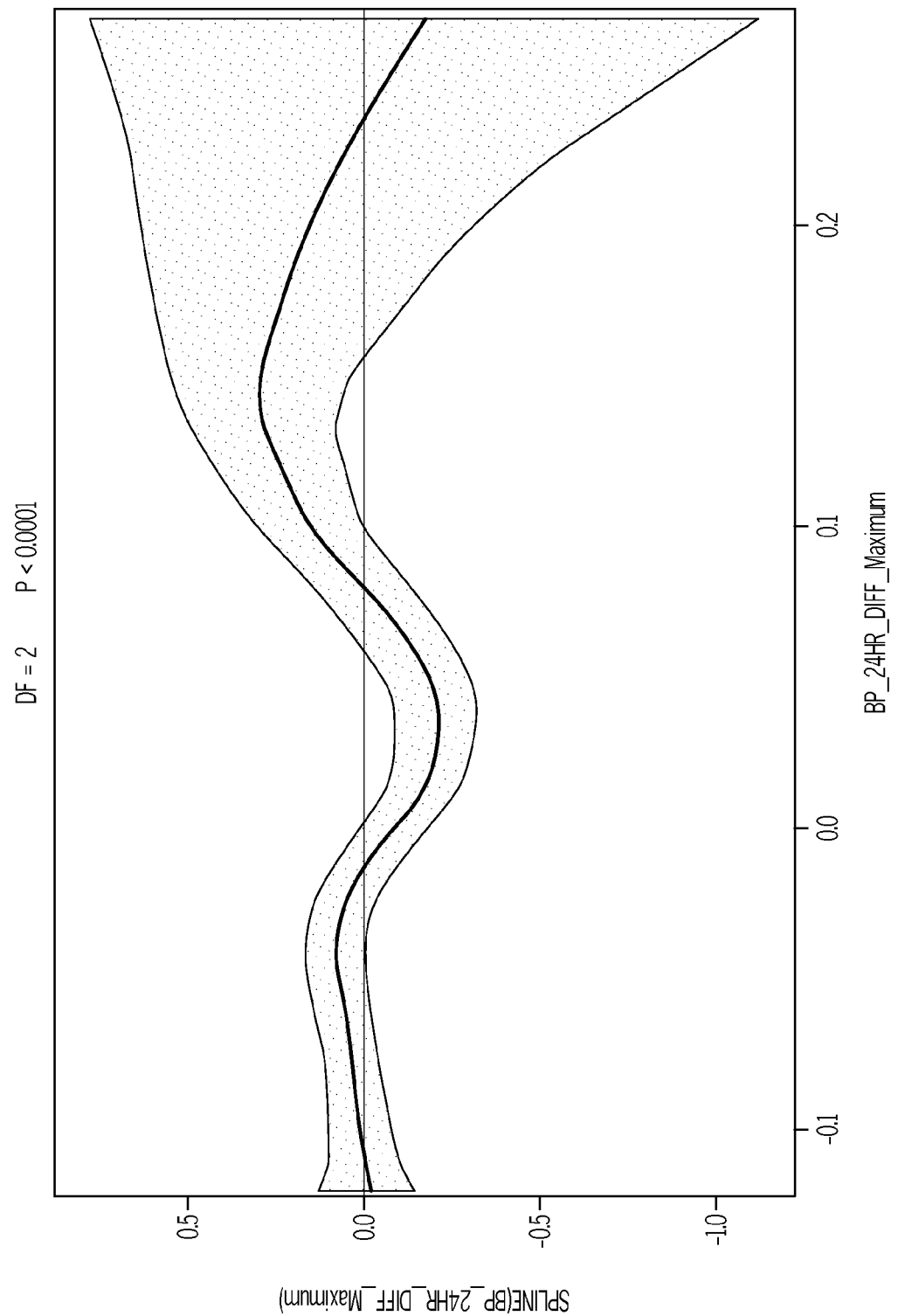
FIG. 8. 8A) Generalized Additive Model (GAM) based on the original data set for lower BP tertile in the Summer season; 8B) Generalized Estimating Equation model based on the same original data set; 8C) two best Bootstrap Models for re-sampled data.
Figure 9A:
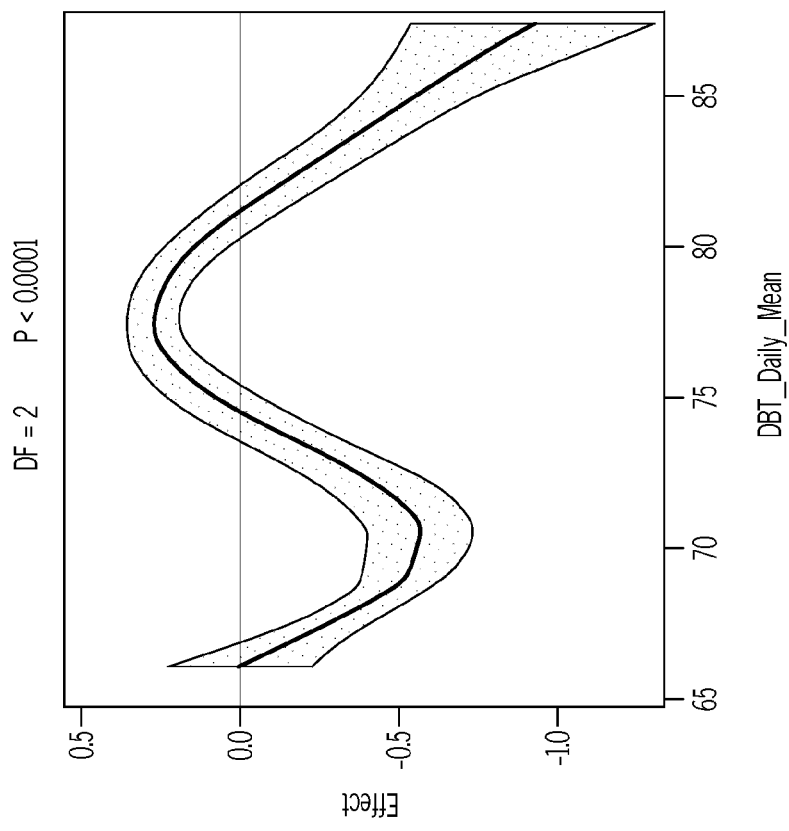
FIG. 9. 9A) Generalized Additive Model (GAM) based on the original data set for middle BP tertile in the Summer season; 9B) Generalized Estimating Equation model based on the same original data set; 9C) two best Bootstrap Models for re-sampled data.
Figure 9A:
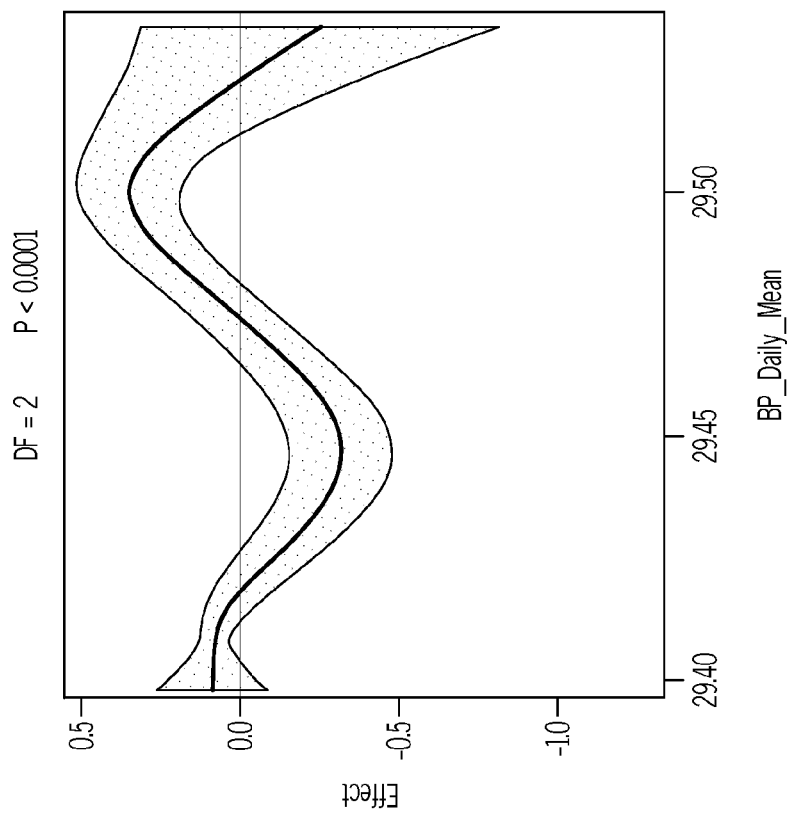
Figure 10A:
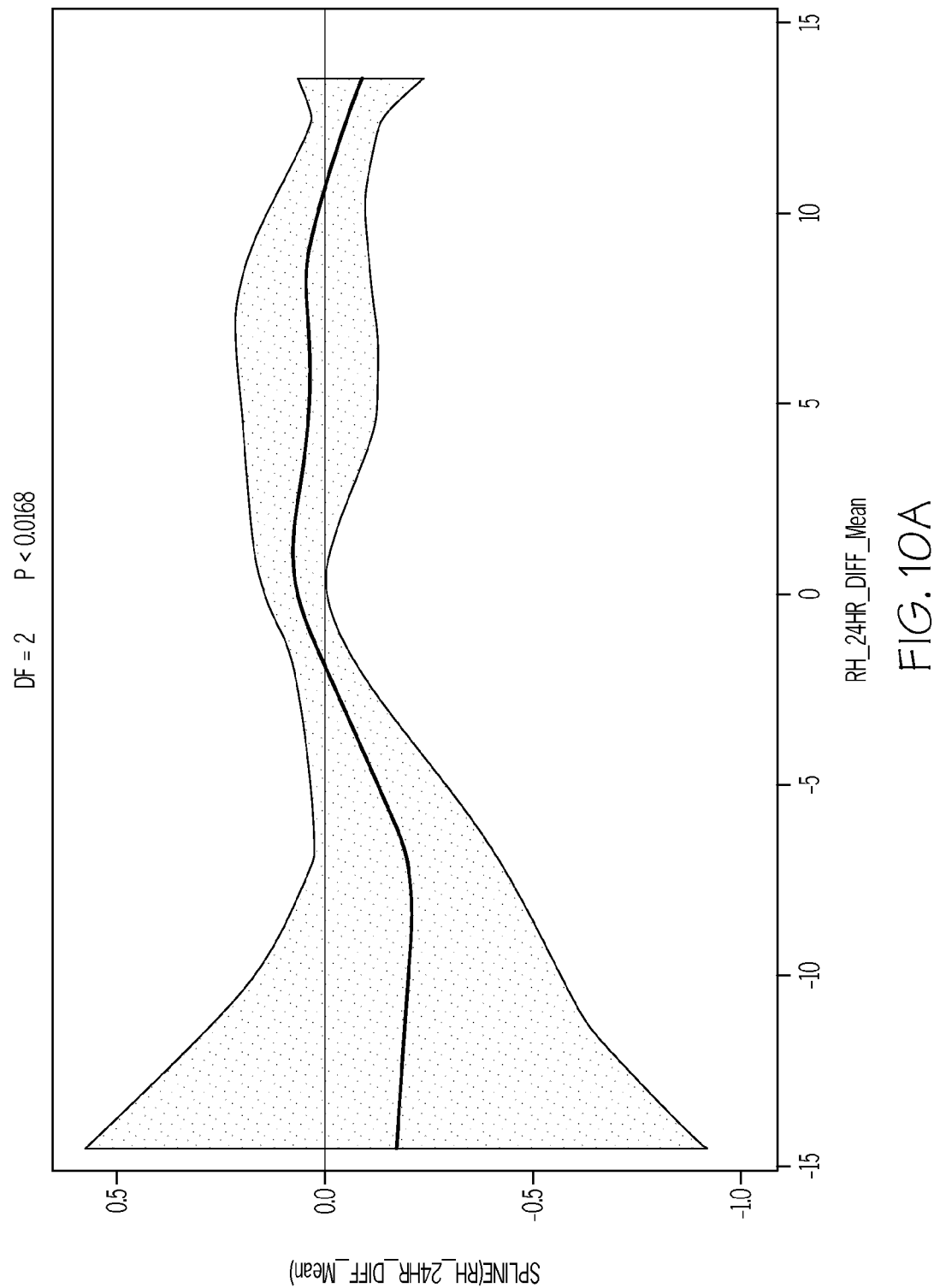
FIG. 10. 10A) Generalized Additive Model (GAM) based on the original data set for upper BP tertile in the Summer season; 10B) Generalized Estimating Equation model based on the same original data set; 10C) two best Bootstrap Models for re-sampled data.

The following example utilizes a bootstrap analysis to provide initial validation for the optimal models developed for the Lower, Middle and Upper BP days for the Summer season.
Previously, we had observed that the best variables for the Lower, Middle, and Upper BP tertile days were as follows:
Lower BP→1) BP 24-hour difference Max
Middle BP→1) BP Daily Mean+2) DBT Daily Mean
Upper BP→1) RH 24-hour Difference Mean For each BP tertile, a generalized additive model (GAM) using the original data set was performed to observe the potential cut-points for each variable (FIGS. 8A, 9A and 10A), for lower, middle and upper BP tertile respectively. Then, a GEE regression analysis was performed for our "best" cut-point model using the original data set (FIGS. 8B, 9B and 10B).

Based on the potential cut-points from the GAM analyses, several GEE analyses using the bootstrap data sets were performed using different combinations of cut-points for the two variables. For each BP tertile, 1,000 bootstrap data sets were generated. The GEE regression analysis was performed for each bootstrap data set. Based on the results of the 1,000 data sets, the bootstrap 95% confidence intervals were determined for each statistic in the GEE regression.

The following cut-point combinations were assessed in the bootstrap analysis:

| Lower BP | Middle BP | Upper BP |
|---|---|---|
| BP ≤ 0.01 | BP ≤ 29.42, DBT ≤ 71 | RH ≥ −2 |
| BP ≤ 0.00 | BP ≤ 29.42, DBT ≤ 74 | RH ≥ 0 |
| BP ≤ 0.05 | BP ≤ 29.42, DBT ≤ 77 | RH ≥ 5 |
| BP ≤ 0.09 | BP ≤ 29.44, DBT ≤ 71 | RH ≥ 7 |
| BP ≤ 0.10 | BP ≤ 29.44, DBT ≤ 74 | |
| | BP ≤ 29.44, DBT ≤ 77 | |
| | BP ≤ 29.475, DBT ≤ 71 | |
| | BP ≤ 29.475, DBT ≤ 74 | |
| | BP ≤ 29.475, DBT ≤ 77 | |

Results for each combination of cut-points were compared and the "best" bootstrap models were selected. The output for the best models are summarized in FIGS. 8C, 9C and 10C for lower, middle and upper BP tertile days, respectively. For each predictor variable, the output consists of the mean value and 95% confidence interval for the following statistics: the RR estimate, the Lower Cl of the RR, the Upper Cl of the RR, the p-value estimate, and the QIC fit statistic estimate.

For example, in the analysis of the Lower BP days there were two models selected as "best." Model 1 (FIG. 8C) involved using the cut-points of BP 24-hour difference Max≥−0.01. The mean RR estimate for the BP variable across the 1,000 bootstrap data sets was 3.82. The 95% confidence interval for this RR estimate across the 1,000 bootstrap data sets was (3.19, 4.62). The mean estimate of the Lower Cl for the RR of the BP variable was 1.54 with a 95% Cl of (1.32, 1.77), across the 1,000 bootstrap data sets. The other results for the other statistics can be interpreted in a similar fashion.

Example 9

This example illustrates how an individual patient who suffers from weather-associated migraine headaches can utilize a predictive model according to the some embodiments of the invention to manage mitigating and preventative treatment. Patient A suffers from migraines. Patient A is planning an important schedule item on Aug. 2, 2015. Patient A wants to know the likelihood that she will suffer a migraine headache on Aug. 2, 2015. Patient A lives in Lexington, Ky., which is climate region Cfa, and the season is Summer. Predicted hourly weather data, including BP, RH, DBT WD and WS are gathered for August 1 and August 2. The predicted BP for August 2 is determined and August 2 is classified as an upper, middle or lower BP tertile day. The appropriate equation is selected based on BP tertile, season and climate region; weather variable data for the appropriate model equation are entered, and the risk is determined. If the risk is greater than 50%, Patient A begins taking preventative medication on August 1.

In some embodiments, the model equations may be generated from population data and weather data for the climate region across a time frame that includes all relevant seasons of the climate region. In more individualized regimens, model equations may generated from individual data and weather data for a climate region across a time frame that includes all relevant seasons of the climate region. In some embodiments the equations are dynamic and evolve in accordance with entered data on a continuous basis. In specific embodiments a program implementing a population data-generated model equation may be adaptable in response to user input of individual data such that the model automatically updates and conforms to the most recent entered data.

Predictive model equations according to embodiments of the invention may be generated similarly for any disease or medical condition which is weather-associated with respect to manifestation of symptoms. Population models, which are generally applicable to an individual in the model-specific climate region, may be generated by gathering symptom/flare-up/onset data for a patient cohort across a time frame that includes the seasons relevant to the climate region (for example, it is contemplated that data collected in the Koppen-Geiger climate classifications A and E may be subject to one relevant season, while data collected in classifications B, C and D may be subject to multiple relevant seasons depending on the medical condition/disease sensitivity to a season affect). Hourly weather data is gathered across the same time frame. Data includes, for example, the max, min, mean of barometric pressure, relative humidity, dew point temperature, dry bulb temperature, wind direction, wind speed, precipitation, and differentials of all weather parameters. The days are identified for a relevant season and the days within each season are placed into quantiles (in specific embodiments, tertiles) based on mean daily BP so that there is at least an upper, lower and middle quantile. Models are generated according to embodiments of the invention and the season and BP quantile are used to determine the appropriate model. To predict risk on a future day, the season and predicted BP quantile are used to select the appropriate model for a given climate region, and weather data gathered for the future day and the day immediately prior to the future day (in order to determine differentials) are entered into the equations and a risk is assessed. The patient may then initiate mitigating or preventative treatment to reduce the risk, or utilize the risk assessment to schedule around high-risk days.

It is expressly contemplated that each of the various aspects, embodiments, and features thereof described herein may be freely combined with any or all other aspects, embodiments, and features. The resulting aspects and embodiments (e.g., models and methods) are within the scope of the invention. It should be understood that headings herein are provided for purposes of convenience and do not imply any limitation on content included below such heading or the use of such content in combination with content included below other headings.

All articles, books, patent applications, patents, other publications mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim may be modified to include one or more elements, limitations, clauses, or descriptive terms, found in any other claim that is dependent on the same base claim. Furthermore, where the claims recite a product, it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) may be removed from the group. The invention provides all such embodiments.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments of the invention, to the tenth of the unit of the lower limit of the range, unless the context clearly dictates otherwise. Any one or more embodiment(s), element(s), feature(s), aspect(s), component(s) etc., of the present invention may be explicitly excluded from any one or more of the claims.

Those skilled in the art will recognize, or be able to ascertain using no more than routine experimentation, many equivalents to the specific embodiments of the invention described and exemplified herein. The scope of the present invention is not intended to be limited to the above Description and Examples, but rather is as set forth in the appended claims.

Computer Program for Generating Model Equations According to Particular Embodiments of the Invention:

```
Libname weather '\\tsclient\E\Mark Simmons Documents\Dr. Martin\Analysis for
2013'; Run;
Libname old '\\tsclient\E\Mark Simmons Documents\Dr. Martin\Analysis for 2012';
Run;
Libname weather2 '\\tsclient\E\Mark Simmons Documents\Dr. Martin\Analysis for
2014'; Run;
Data Subject; Set weather.Wxmx_master_withid;
Keep Date ID NOH_Today ADJ_NOH_Today HA_Today NOH ADJ_NOH ; Run;
Data Subject_Age; Set old.headache_data_revised; Keep ID Age; Run;
Data Subject_Age; Set Subject_Age; If Age = . Then delete; Run;
Data Subject_Age; Set Subject_Age; If ID = 1001 Then Age = 58; Run;
```

-continued

```
Proc Sort Data=Subject_Age NoDup; By _all_; Run;
Data Daily; Set weather.NOH_revised_2;
Keep Date Season NOH_Daily_Proportion ADJ_NOH_Daily_Proportion
ANYHA_Daily_Proportion
N_NOH N_ADJNOH N_ANYHA NOH_denom HA_ADJ_NOH_numerator NOH_num
Recalc_Adj_NOH Season_Number
Upper_Tertile_SeasonAdj_1 Upper_Tertile_SeasonAdj_2 Upper_Tertile_SeasonAdj_3
Upper_Tertile_SeasonAdj_4 Upper_Tertile_SeasonAdj_5
Upper_Half_Fall Upper_Half_Winter Upper_Half_Spring Upper_Half_Summer
BPMean_BP24Diff Description_of_BPMean_BP24Diff
BP_Daily_Mean BP_24Hr_Diff_Mean BP_24Hr_Diff_Maximum
DBT_Daily_Mean RH_Daily_Mean RH_24HR_DIFF_Minimum WS_24HR_DIFF_Maximum ;
Run;
Data Lightning; Set weather.lightning;
Keep Date Lightning_Current_mean -- FreqGreater_Neg8_8_median ; Run;
Proc Sort Data=Daily; By Date; Run;
Proc Sort Data=Lightning; By Date; Run;
Data Daily_2; Merge Lightning Daily; By Date; Run;
Proc Sort Data=Daily_2; By descending Date; Run;
Data Daily_3; Set Daily_2; Next_day_Lightning = LAG1(TotalLightningFreq_median);
Run;
Proc Sort Data=Daily_3; By Date; Run;
Data Daily_4; Set Daily_3; Prev_day_Lightning = LAG1(TotalLightningFreq_median);
Run;
Data Daily_4; Set Daily_4;
Length Today_Lightning_group $ 14 ;
Length Previous_day_Lightning_group $ 14 ;
Length Next_day_Lightning_group $ 14 ;
If TotalLightningFreq_median = 0                        Then Today_Lightning_group = "Zero";
If TotalLightningFreq_median gt 0 AND TotalLightningFreq_median lt 18 Then
Today_Lightning_group = "First Tertile";
If TotalLightningFreq_median ge 18 AND TotalLightningFreq_median le 220 Then
Today_Lightning_group = "Second Tertile";
If TotalLightningFreq_median gt 220             Then Today_Lightning_group =
"Third Tertile";
If Prev_day_Lightning = 0                       Then
Previous_day_Lightning_group = "Zero";
If Prev_day_Lightning gt 0 AND Prev_day_Lightning lt 18      Then
Previous_day_Lightning_group = "First Tertile";
If Prev_day_Lightning ge 18 AND Prev_day_Lightning le 220    Then
Previous_day_Lightning_group = "Second Tertile";
If Prev_day_Lightning gt 220                    Then
Previous_day_Lightning_group = "Third Tertile";
If Next_day_Lightning = 0                       Then
Next_day_Lightning_group = "Zero";
If Next_day_Lightning gt 0 AND Next_day_Lightning lt 18      Then
Next_day_Lightning_group = "First Tertile";
If Next_day_Lightning ge 18 AND Next_day_Lightning le 220    Then
Next_day_Lightning_group = "Second Tertile";
If Next_day_Lightning gt 220                    Then
Next_day_Lightning_group = "Third Tertile";
Fraction_lightning_SQRT = SQRT(Fraction_with_lightning);
Lightning_freq_SQRT = SQRT(TotalLightningFreq_median); Run;
Data Daily_4; Set Daily_4;
If Season_Number = 1 AND Date ge '01Aug2009'd AND Recalc_Adj_NOH le 0.35 Then
Upper_Half_Summer_1 = 0;
If Season_Number = 1 AND Date ge '01Aug2009'd AND Recalc_Adj_NOH gt 0.35 Then
Upper_Half_Summer_1 = 1;
Rename Upper_Half_Summer = Upper_Half_Summer_2; Run;
Data Daily_4; Set Daily_4;
If Season_Number = 1 AND Date ge '01Aug2009'd AND Recalc_Adj_NOH le 0.4166667
Then Upper_Quartile_Summer_1 = 0;
If Season_Number = 1 AND Date ge '01Aug2009'd AND Recalc_Adj_NOH gt 0.4166667
Then Upper_Quartile_Summer_1 = 1;
If Season_Number = 2 AND Recalc_Adj_NOH le 0.3666667 Then Upper_Quartile_Fall =
0;
If Season_Number = 2 AND Recalc_Adj_NOH gt 0.3666667 Then Upper_Quartile_Fall =
1;
If Season_Number = 3 AND Recalc_Adj_NOH le 0.3191489 Then Upper_Quartile_Winter
= 0;
If Season_Number = 3 AND Recalc_Adj_NOH gt 0.3191489 Then Upper_Quartile_Winter
= 1;
If Season_Number = 4 AND Recalc_Adj_NOH le 0.2959785 Then Upper_Quartile_Spring
= 0;
If Season_Number = 4 AND Recalc_Adj_NOH gt 0.2959785 Then Upper_Quartile_Spring
= 1;
If Season_Number = 5 AND Recalc_Adj_NOH le 0.3062500 Then
Upper_Quartile_Summer_2 = 0;
If Season_Number = 5 AND Recalc_Adj_NOH gt 0.3062500 Then
```

```
Upper_Quartile_Summer_2 = 1; Run;
Proc Sort Data=Subject; By ID; Run;
Proc Sort Data=Subject_Age; By ID; Run;
Data Subject_2; Merge Subject_Age Subject; By ID; Run;
Proc Means Data=Subject_2 NoPrint; Title "Calculating the Mean Age of the all
the subjects reporting on a given Date";
Class Date; Var Age; Output OUT=Mean_Age Mean=Daily_Mean_Age ; Run;
Data Mean_Age_2; Set Mean_Age; Keep Date Daily_Mean_Age; Run;
Proc Sort Data=Mean_Age_2; By Date; Run;
Proc Sort Data=Subject_2; By Date; Run;
Data Subject_3; Merge Mean_Age_2 Subject_2; By Date; Run;
Proc Sort Data=Subject_3; By Date ; Run;
Proc Sort Data=Daily_4; By Date ; Run;
Data NOH_revised_with_IDs; Merge Subject_3 Daily_4; By Date; Run;
Data NOH_revised_with_IDs; Set NOH_revised_with_IDs;
LN_N = LOG(N_ADJNOH);
If TotalLightningFreq_median gt 0 Then Lightning_Today = 1;        Else
Lightning_Today = 0;
If TotalLightningFreq_median gt 0 OR Next_day_Lightning gt 0       Then
Lightning_today_or_tomorrow = 1; Else Lightning_today_or_tomorrow = 0;
If Today_Lightning_group = "Second Tertile" OR Today_Lightning_group = "Third
Tertile"   Then Today_Lightning_group_2_3 = 1;         Else
Today_Lightning_group_2_3 = 0;
If Today_Lightning_group = "Second Tertile" OR Today_Lightning_group = "Third
Tertile" OR
       Next_day_Lightning_group = "Second Tertile" OR Next_day_Lightning_group =
"Third Tertile"
Then Today_Tom_Lightning_group_2_3 = 1; Else Today_Tom_Lightning_group_2_3 = 0;
Run;
Data Fall_Winter_Spring_2; Set NOH_revised_with_IDs;
If Season_Number = 2 OR Season_Number = 3 OR Season_Number = 4 Then output
Fall_Winter_Spring_2; Run;
Data Fall_Winter_Spring_2; Set Fall_Winter_Spring_2;
If Upper_Tertile_SeasonAdj_2 = 1 OR Upper_Tertile_SeasonAdj_3 = 1 OR
Upper_Tertile_SeasonAdj_4 = 1
       Then Upper_Tertile_FWS = 1; Else Upper_Tertile_FWS = 0;
If Upper_Half_Fall=1 OR Upper_Half_Winter=1 OR Upper_Half_Spring=1 Then
Upper_Half_FWS=1; Else Upper_Half_FWS=0;
If Upper_Quartile_Fall = 1 OR Upper_Quartile_Winter = 1 OR
Upper_Quartile_Spring = 1
       Then Upper_Quartile_FWS = 1; Else Upper_Quartile_FWS = 0; Run;
Data Summer_both; Set NOH_revised_with_IDs; If Season_Number = 1 OR
Season_Number = 5 Then output Summer_both; Run;
Data Summer_both; Set Summer_both; If Date lt '01Aug2009'd Then delete; Run;
Data Summer_both; Set Summer_both;
If Upper_Tertile_SeasonAdj_1=1 OR Upper_Tertile_SeasonAdj_5=1 Then
Upper_Tertile_Summer_both=1; Else Upper_Tertile_Summer_both=0;
If Upper_Half_Summer_1=1 OR Upper_Half_Summer_2=1 Then
Upper_Half_Summer_both=1; Else Upper_Half_Summer_both=0;
If Upper_Quartile_Summer_1 = 1 OR Upper_Quartile_Summer_2 = 1 Then
Upper_Quartile_Summer_both = 1; Else Upper_Quartile_Summer_both = 0; Run;
Data FWS_Low_BP; Set Fall_Winter_Spring_2;
If BPMean_BP24Diff = 1 OR BPMean_BP24Diff = 2 OR BPMean_BP24Diff = 3 Then
output FWS_Low_BP; Run;
Data FWS_Avg_BP; Set Fall_Winter_Spring_2;
If BPMean_BP24Diff = 4 OR BPMean_BP24Diff = 5 OR BPMean_BP24Diff = 6 Then
output FWS_Avg_BP; Run;
Data FWS_High_BP; Set Fall_Winter_Spring_2;
If BPMean_BP24Diff = 7 OR BPMean_BP24Diff = 8 OR BPMean_BP24Diff = 9 Then
output FWS_High_BP; Run;
Data Summer_both_Low_BP;   Set Summer_both;
If BPMean_BP24Diff = 1 OR BPMean_BP24Diff = 2 OR BPMean_BP24Diff = 3 Then
output Summer_both_Low_BP; Run;
Data Summer_both_Avg_BP;   Set Summer_both;
If BPMean_BP24Diff = 4 OR BPMean_BP24Diff = 5 OR BPMean_BP24Diff = 6 Then
output Summer_both_Avg_BP; Run;
Data Summer_both_High_BP;   Set Summer_both;
If BPMean_BP24Diff = 7 OR BPMean_BP24Diff = 8 OR BPMean_BP24Diff = 9 Then
output Summer_both_High_BP; Run;
    Data FWS_Low_BP_3; Set FWS_Low_BP;
       If BP_24Hr_Diff_Mean le −0.10          Then BP_Diff_Mean_Low = 1;
       If BP_24Hr_Diff_Mean gt −0.10          Then BP_Diff_Mean_Low = 0;
       If BP_24Hr_Diff_Mean = .               Then BP_Diff_Mean_Low = .;
       If WS_24HR_DIFF_Maximum lt 7      Then WS_Diff_Max_ge_7 = 0;
       If WS_24HR_DIFF_Maximum ge 7      Then WS_Diff_Max_ge_7 = 1;
       If WS_24HR_DIFF_Maximum = .       Then WS_Diff_Max_ge_7 = .;
       Run;
       Proc GenMod Data=FWS_Low_BP_3 ;
          Class ID Date BP_Diff_Mean_Low (ref="0" param=ref)    WS_Diff_Max_ge_7
```

```
(ref="0" param=ref) ;
    Model Upper_Tertile_FWS = BP_Diff_Mean_Low WS_Diff_Max_ge_7 /
dist=poisson link=log offset=LN_N ;
    Repeated subject=Date / type=ind within=ID;
    Estimate 'RR for BP_24Hr_Diff_Mean_Low, Yes vs No'    BP_Diff_Mean_Low
1.0 / exp;
    Estimate 'RR for WS_24HR_Diff_Max_ge_7, Yes vs. No' WS_Diff_Max_ge_7
1.0 / exp;
    Run; Quit;
    Data FWS_Avg_BP_5; Set FWS_Avg_BP;
        If BP_24Hr_Diff_Mean le −0.05      Then BP_24hr_Mean_Group = 1;
        If BP_24Hr_Diff_Mean gt −0.05      Then BP_24hr_Mean_Group = 2;
        If BP_24Hr_Diff_Mean = .           Then BP_24hr_Mean_Group = .;
        If RH_Daily_Mean lt 79             Then RH_Daily_Mean_Group = 1;
        If RH_Daily_Mean ge 79             Then RH_Daily_Mean_Group = 2;
        If RH_Daily_Mean = .               Then RH_Daily_Mean_Group = .;
    Run;
    Proc GenMod Data=FWS_Avg_BP_5 ;
        Class ID Date BP_24hr_Mean_Group (ref="2" param=ref)
RH_Daily_Mean_Group (ref="1" param=ref) ;
    Model Upper_Tertile_FWS = BP_24hr_Mean_Group RH_Daily_Mean_Group /
dist=poisson link=log offset=LN_N ;
    Repeated subject=Date / type=ind within=ID;
    Estimate 'RR for BP_24Hr_Diff_Mean_Group, 1 vs 2'     BP_24hr_Mean_Group
1.0 / exp;
    Estimate 'RR for RH_Daily_Mean_Group, 2 vs 1 '       RH_Daily_Mean_Group
1.0 / exp;
    Run;   Quit ;
%MACRO FWS_High (Var1=, Var2=, Var3=, Var4=) ;
Data FWS_High_BP_8; Set FWS_High_BP;
If &Var1 lt &Var2         Then Group_A = 1;
If &Var1 ge &Var2         Then Group_A = 2;
If &Var1 = .              Then Group_A = .;
If &Var3 le &Var4         Then Group_B = 1;
If &Var3 gt &Var4         Then Group_B = 2;
If &Var3 = .              Then Group_B = .;
Run;
Proc GenMod Data=FWS_High_BP_8 ;
Class ID Date Group_A (ref="1" param=ref) Group_B (ref="2" param=ref) ;
Model Upper_Tertile_FWS = Group_A Group_B / dist=poisson link=log offset=LN_N
;
Repeated subject=Date / type=ind within=ID;
Estimate "RR for Group_A, 2 vs 1 ('&Var1' ge '&Var2' vs lt '&Var2')"   Group_A
    1.0 / exp;
Estimate "RR for Group_A, 1 vs 2 ('&Var3' le '&Var4' vs gt '&Var4')"   Group_B
    1.0 / exp;
Run; Quit;
%MEND;
%FWS_High ( Var1 = BP_24HR_Diff_Mean, Var2 = 0.10,      Var3 =
RH_24HR_Diff_Minimum, Var4 = −25 );
    Data Summer_Low_2; Set Summer_both_Low_BP;
        If BP_24Hr_Diff_Maximum le 0.00    Then BP_24hr_Max_cutpoint = 1;
        If BP_24Hr_Diff_Maximum gt 0.00    Then BP_24hr_Max_cutpoint = 0;
        If BP_24Hr_Diff_Maximum = .        Then BP_24hr_Max_cutpoint = .;
    Run;
    Proc GenMod Data=Summer_Low_2 ;
        Class ID Date BP_24hr_Max_cutpoint (ref="0" param=ref) ;
        Model Upper_Tertile_Summer_both = BP_24hr_Max_cutpoint / dist=poisson
link=log offset=LN_N type3;
        Repeated subject=Date / type=ind within=ID;
        Estimate "RR for BP_24Hr_Max_cutpoint le 0.0, Yes vs No"
BP_24hr_Max_cutpoint 1.0 / exp;
    Run; Quit;
    Data Summer_Avg_1; Set Summer_both_Avg_BP;
        If BP_Daily_Mean le 29.44          Then BP_Daily_Mean_cutpoint = 1;
        If BP_Daily_Mean gt 29.44          Then BP_Daily_Mean_cutpoint = 0;
        If BP_Daily_Mean = .               Then BP_Daily_Mean_cutpoint = .;
        If DBT_Daily_Mean le 77            Then DBT_Daily_Mean_cutpoint = 1;
        If DBT_Daily_Mean gt 77            Then DBT_Daily_Mean_cutpoint = 0;
        If DBT_Daily_Mean = .              Then DBT_Daily_Mean_cutpoint = .;
    Run;
Proc GenMod Data=Summer_Avg_1 ;
Class ID Date BP_Daily_Mean_cutpoint (ref="0" param=ref)
DBT_Daily_Mean_cutpoint (ref="0" param=ref) ;
Model Upper_Tertile_Summer_both=BP_Daily_Mean_cutpoint DBT_Daily_Mean_cutpoint /
dist=poisson link=log offset=LN_N type3;
Repeated subject=Date / type=ind within=ID;
Estimate "RR for BP_Daily_Mean_cutpoint le 29.44, Yes vs No"
BP_Daily_Mean_cutpoint 1.0 / exp;
```

```
Estimate "RR for DBT_Daily_Mean_cutpoint le 77, Yes vs No"
DBT_Daily_Mean_cutpoint 1.0 / exp;
Run; Quit;
    Data Summer_High_4; Set Summer_both_High_BP;
    If RH_Daily_Mean lt 76    Then RH_Daily_Mean_Group = 0;
    If RH_Daily_Mean ge 76    Then RH_Daily_Mean_Group = 1;
    If RH_Daily_Mean = .      Then RH_Daily_Mean_Group = .;
    Run;
    Proc GenMod Data=Summer_High_4 ;
    Class ID Date RH_Daily_Mean_Group (ref="0" param=ref) ;
    Model Upper_Tertile_Summer_both = RH_Daily_Mean_Group / dist=poisson
link=log offset=LN_N type3;
    Repeated subject=Date / type=ind within=ID;
    Estimate "RR for RH_Daily_Mean_Group ge 76, Yes vs No"
    RH_Daily_Mean_Group 1.0 / exp;
    Run; Quit;
```

What is claimed:

1. A method of reducing a risk of a subject residing in climate region Cfa and predisposed to experiencing weather-associated adverse events for experiencing a new onset migraine headache (NOH) on a given day, the method comprising:
   a) determining a relevant season in which the given day falls;
   b) determining whether the given day is an upper, middle or lower barometric pressure (BP) tertile day;
   c) selecting an equation specific to the determined relevant season and the determined BP tertile from the group consisting of:

$$[\text{season}=W, BP \text{ tertile}=\text{low}] R = e^{[\beta_0 + \beta_1 A + \beta_2 B]} + N + \varepsilon \text{ or}$$
   $$1 = e^{[\beta_0 + \beta_1 A + \beta_2 A(exp)2 + \beta_3 B + \beta_4 B(exp)2]} + N + \varepsilon \quad (1)$$

$$[\text{season}=W, BP \text{ tertile}=\text{mid}] R = e^{[\beta_0 + \beta_1 A + \beta_2 B]} + N + \varepsilon \quad (2)$$

$$[\text{season}=W, BP \text{ tertile}=\text{high}] R = e^{[\beta_0 + \beta_1 A + \beta_2 C]} + N + \varepsilon \quad (3)$$

$$[\text{season}=S, BP \text{ tertile}=\text{low}] R = e^{[\beta_0 + \beta_1 E]} + N + \varepsilon \quad (4)$$

$$[\text{season}=S, BP \text{ tertile}=\text{mid}] R = e^{[\beta_0 + \beta_1 G + \beta_2 F]} + N + \varepsilon \quad (5)$$

$$[\text{season}=S, BP \text{ tertile}=\text{high}] R = e^{[\beta_0 + \beta_1 H]} + N + \varepsilon \quad (6)$$

wherein
   R=risk of a given day being a upper tertile incident rate new onset headache day (UT-IR-NOH);
   N=number of subjects in a cohort eligible to have a NOH on a given day and is a denominator in an IR-NOH calculation;
   A=BP 24 hour differential mean;
   B=wind speed (WS) 24 hour differential maximum;
   C=dry bulb temperature (DBT) 24 hour differential mean;
   E=BP 24 hour differential maximum;
   F=DBT daily mean;
   G=BP daily mean;
   H=relative humidity (RH) 24 hour differential mean; and
   $\varepsilon$=an error term of GEE regression modeling;
   d) entering weather variable data for the given day into the selected equation to yield an assessment of the risk; and
   e) administering a migraine headache prophylactic treatment to the subject when the risk of experiencing a new onset migraine headache is assessed as greater than 50%.

2. The method according to claim 1, wherein the subject cohort is further controlled according to factors known to influence frequency of a medical condition precipitating the adverse event associated with the weather.

3. The method according to claim 2, wherein the factors are selected from race, gender, age, socio-economic status and combinations thereof.

4. The method according to claim 1, wherein the prophylactic treatment is selected from the group consisting of beta blockers, propranolol, calcium channel blockers, angiotensin-converting enzyme inhibitors, antidepressants, anti-seizure drugs, and pain relievers.

* * * * *